United States Patent
Shamanin et al.

(10) Patent No.: US 6,562,597 B2
(45) Date of Patent: May 13, 2003

(54) PAPILLOMA VIRUSES, AGENTS FOR DETECTING THEM AND FOR TREATING DISEASES CAUSED BY SUCH VIRUSES

(75) Inventors: Vladimir Shamanin, Heidelberg (DE); Ethel-Michele De Villiers-Zur Hausen, Waldmichelbach (DE); Harald Zur Hausen, Waldmichelbach (DE)

(73) Assignee: Deutsches Krebsforschungszentrum Stiftung des Offentlichen Rechts, Heidelberg (DE)

( * ) Notice: Subject to any disclaimer, the term of this patent is extended or adjusted under 35 U.S.C. 154(b) by 0 days.

(21) Appl. No.: 10/056,359

(22) Filed: Jan. 23, 2002

(65) Prior Publication Data

US 2002/0110865 A1 Aug. 15, 2002

Related U.S. Application Data

(62) Division of application No. 09/628,099, filed on May 25, 2000, now Pat. No. 6,368,832, which is a division of application No. 09/000,266, filed as application No. PCT/DE96/01369 on Jul. 19, 1996, now Pat. No. 6,322,795.

(30) Foreign Application Priority Data

Jul. 19, 1995 (DE) .......................... 195 26 386

(51) Int. Cl.$^7$ .......................... C12P 21/06; C12N 15/00
(52) U.S. Cl. .................... 435/69.3; 435/69.1; 435/91.1; 435/91.33; 530/350; 530/403; 530/300; 536/23.72; 424/204.1
(58) Field of Search .............................. 435/69.3, 69.1, 435/5, 91.1, 91.33, 7.1; 424/204.1; 530/300, 350, 403; 536/23.72

(56) References Cited

FOREIGN PATENT DOCUMENTS

| DE | A44 15 743 | 11/1995 |
|----|-----------|---------|
| EP | A0 301 289 | 2/1989 |
| EP | A0 370 625 | 5/1990 |
| WO | WOA94 05792 | 3/1994 |

OTHER PUBLICATIONS

Browne et al., 1988, "Analysis of the L1 Gene Product of Human Papillomavirus Type 16 by Expression in a Vaccinia Virus Recombinant," *J. Gen. Virology* 69: 1263–1273.

Egawa et al., 1993, "Two Novel Types of Human Papillomavirus, HPV 63 and HPV 65: Comparisons of their Clinical and Histological Features and DNA Sequences to Other HPV Types," *Virology* 194:789–799.

Hagensee et al., 1993, "Self–Assembly of Human Papillomavirus Type 1 Capsids by Expression of the L1 Protein Alone or by Coexpression of the L1 and L2 Capsid Proteins," *Journal of Virology* 67:315–322.

Jarrett et al., 1991, "Studies on Vaccination Against Papillomaviruses: Prophylactic and Therapeutic Vaccination with Recombinant Structural Protein," *Virology* 184:33–42.

Kirnbauer et al., 1993, "Efficient Self–Assembly of Human Papillomavirus Type 16 L1 and L1–L2 into Virus–Like Particles," *Journal of Virology* 67: 6929–6936.

Shamanin et al., 1994, "Specific Types of Human Papillomavirus Found in Benign Proliferations and Carcinomas of the Skin in Immunosuppressed Patients," *Cancer Research* 54:4610–4613.

Shamanin et al., 1996, "Human Papillomavirus Infections in Nonmelanoma Skin Cancer from Renal Transplant Recipients and Nonimmunosuppressed Patients," *Journal of the National Cancer Institute* 88(12):802–811.

Syrjänen, K.J., 1980, "Bronchial Squamous Cell Carcinomas Associated with Epithelial Changes Identical to Condylomatous Lesions of the Uterine Cervix," *Lung* 158:131–142.

zur Hausen, H., 1976, "Biochemical Approaches to Detection of Epstein–Barr Virus in Human Tumors," *Cancer Research* 36:678–680.

zur Hausen, H., 1976, "Condylomata Acuminata and Human Genital Cancer," *Cancer Research* 36:794.

zur Hausen, H., 1989, "Papillomaviruses in Anogenital Cancer as a Model to Understand the Role of Viruses in Human Cancers," *Cancer Research* 49:4677–4681.

Xi et al., J. of Gen. Virology, 1991, vol. 72, pp 2981–2988 (abstract only).

Zhou et al., Virology, 1991, vol. 185, pp 251–257.

Tomita et al., J. of Virology, 1987, vol. 61, pp 2389–2394.

Rose et al., J. of Virology, 1993, vol. 67, pp. 1936–1944.

*Primary Examiner*—Ali R. Salimi
(74) *Attorney, Agent, or Firm*—Pennie & Edmonds LLP

(57) ABSTRACT

This invention relates to a DNA coding for a peptide of a papilloma virus major capsid protein. Moreover, this invention deals with a papilloma virus genome containing such a DNA. Furthermore, this invention concerns proteins coded by the papilloma virus genome and virus-like particles as well as antibodies directed thereagainst and the use thereof for diagnosis, treatment and vaccination.

10 Claims, 10 Drawing Sheets

GGATCCATGCAGGATGGTGACATGTGTGATATAGGATTCGGAGCTTGCAATTTCAGGGCA
    1 ----------+----------+----------+----------+---------+---------+  60
      CCTAGGTACGTCCTACCACTGTACACACTATATCCTAAGCCTCGAACGTTAAAGTCCCGT a       G  S  M  Q  D  G  D  M  C  D  I  G  F  G  A  C  N  F  R  A     -

TTTCAGCAAGATAGGTCAGGTGTTCCTTTAGATATAGTAGATAGTACTTGCAAGTATCCA
   61 ----------+----------+----------+----------+---------+---------+  120
      AAAGTCGTTCTATCCAGTCCACAAGGAAATCTATATCATCTATCATGAACGTTCATAGGT a       F  Q  Q  D  R  S  G  V  P  L  D  I  V  D  S  T  C  K  Y  P     -

GACTTTTTGAAAATGACAAAAGACAAGTATGGTGATGAATGCTTCTTTTTTGGTCGTCGA
  121 ----------+----------+----------+----------+---------+---------+  180
      CTGAAAAACTTTTACTGTTTTCTGTTCATACCACTACTTACGAAGAAAAAACCAGCAGCT a       D  F  L  K  M  T  K  D  K  Y  G  D  E  C  F  F  F  G  R  R     -

GAGCAGTTGTATGCAAGGCATTATTTTACCAGAGCAGGCACAATAGGTGATTCTATTCCA
  181 ----------+----------+----------+----------+---------+---------+  240
      CTCGTCAACATACGTTCCGTAATAAAATGGTCTCGTCCGTGTTATCCACTAAGATAAGGT a       E  Q  L  Y  A  R  H  Y  F  T  R  A  G  T  I  G  D  S  I  P     -

ACGCCATATCAGGAATCTGAATTTTACAGATCTCCACAGGATAGCCAGGCTCAGAATAAT
  241 ----------+----------+----------+----------+---------+---------+  300
      TGCGGTATAGTCCTTAGACTTAAAATGTCTAGAGGTGTCCTATCGGTCCGAGTCTTATTA a       T  P  Y  Q  E  S  E  F  Y  R  S  P  Q  D  S  Q  A  Q  N  N     -

GTGGATTCTCACATTTATGTAGCCACTCCTAGTGGTTCTTTAACTAGCAGTGATGCTCAG
  301 ----------+----------+----------+----------+---------+---------+  360
      CACCTAAGAGTGTAAATACATCGGTGAGGATCACCAAGAAATTGATCGTCACTACGAGTC a       V  D  S  H  I  Y  V  A  T  P  S  G  S  L  T  S  S  D  A  Q     -

CTGTTTAACAGACCTTATTGGCTCCAAAATGCTCAAGGTACCAATAACGGAATGGATCC
  361 ----------+----------+----------+----------+---------+---------   419
      GACAAATTGTCTGGAATAACCGAGGTTTTACGAGTTCCATGGTTATTGCCTTACCTAGG a       L  F  N  R  P  Y  W  L  Q  N  A  Q  G  T  N  N  G  M  D       -
```

FIG. 2 vs200-1

```
        GGATCCATGGAGGACGGTGAGATGGCAGACATAGGATATGGTAATCTTAATTTTAAAGCT
    1   ----------+---------+---------+---------+---------+---------+  60
        CCTAGGTACCTCCTGCCACTCTACCGTCTGTATCCTATACCATTAGAATTAAAATTTCGA a         G  S  M  E  D  G  E  M  A  D  I  G  Y  G  N  L  N  F  K  A   -

TTACAGGAAAATAGGCCTGATGTTAGTCTTGATATTGTCAATGAAACCTGCAAATATCCA
   61   ----------+---------+---------+---------+---------+---------+ 120
        AATGTCCTTTTATCCGGACTACAATCAGAACTATAACAGTTACTTTGGACGTTTATAGGT a         L  Q  E  N  R  P  D  V  S  L  D  I  V  N  E  T  C  K  Y  P   -

GATTTTTTGAAGATGCAAAATGATGTTTATGGAGACTCCTGTTTCTTTTTTGCTCGTAGA
  121   ----------+---------+---------+---------+---------+---------+ 180
        CTAAAAAACTTCTACGTTTTACTACAAATACCTCTGAGGACAAAGAAAAAACGAGCATCT a         D  F  L  K  M  Q  N  D  V  Y  G  D  S  C  F  F  F  A  R  R   -

GAGCAATGTTATGCCAGACACTTTTTTGTAAGAGGTGGCAACGTAGGGGATGACATTCCT
  181   ----------+---------+---------+---------+---------+---------+ 240
        CTCGTTACAATACGGTCTGTGAAAAAACATTCTCCACCGTTGCATCCCCTACTGTAAGGA a         E  Q  C  Y  A  R  H  F  F  V  R  G  G  N  V  G  D  D  I  P   -

GGTGAACAAATAGACGCAGGCACATATAAAAATGATTTTTACATTCCAGGAGCATCAGGT
  241   ----------+---------+---------+---------+---------+---------+ 300
        CCACTTGTTTATCTGCGTCCGTGTATATTTTTACTAAAAATGTAAGGTCCTCGTAGTCCA a         G  E  Q  I  D  A  G  T  Y  K  N  D  F  Y  I  P  G  A  S  G   -

CAGACACAAAATAAAATAGGTAACTCCATGTATTTCCCAACAGTTAGTGGCTCATTAGTG
  301   ----------+---------+---------+---------+---------+---------+ 360
        GTCTGTGTTTTATTTTATCCATTGAGGTACATAAAGGGTTGTCAATCACCGAGTAATCAC a         Q  T  Q  N  K  I  G  N  S  M  Y  F  P  T  V  S  G  S  L  V   -

TCTAGTGATGCTCAGCTGTTTAATAGGCCCTACTGGCTCCAACGCGCACAGGGCCACAAC
  361   ----------+---------+---------+---------+---------+---------+ 420
        AGATCACTACGAGTCGACAAATTATCCGGGATGACCGAGGTTGCGCGTGTCCCGGTGTTG a         S  S  D  A  Q  L  F  N  R  P  Y  W  L  Q  R  A  Q  G  H  N   -

AACGGCGTGGATCC
  421   ----------+---- 434
        TTGCCGCACCTAGG a         N  G  V  D   -
```

GGATCCCTAGAGGATGGTGATATGGGTGATATAGGATTTGGGCATGCTAATTTTAGCCGT
    1  ----------+----------+----------+----------+----------+----------+ 60
       CCTAGGGATCTCCTACCACTATACCCACTATATCCTAAACCCGTACGATTAAAATCGGCA a        G  S  L  E  D  G  D  M  G  D  I  G  F  G  H  A  N  F  S  R    -

TTACAAGAAGATAAAGCAGGTGTGCCATTAGAATTAGTGGACACTTTTAGTATATGGCCT
   61  ----------+----------+----------+----------+----------+----------+ 120
       AATGTTCTTCTATTTCGTCCACACGGTAATCTTAATCACCTGTGAAAATCATATACCGGA a        L  Q  E  D  K  A  G  V  P  L  E  L  V  D  T  F  S  I  W  P    -

GACTTTTTACGCATGACCAGTGATATATATGGAGATGCTGTGTTTTTTTGGGGAAAGCGA
  121  ----------+----------+----------+----------+----------+----------+ 180
       CTGAAAAATGCGTACTGGTCACTATATATACCTCTACGACACAAAAAAACCCCTTTCGCT a        D  F  L  R  M  T  S  D  I  Y  G  D  A  V  F  F  W  G  K  R    -

GAACATATGTTTGCCAGACATTTATGGGCAAGAGCTGGAACTATGGGCGACGCTATTCCA
  181  ----------+----------+----------+----------+----------+----------+ 240
       CTTGTATACAAACGGTCTGTAAATACCCGTTCTCGACCTTGATACCCGCTGCGATAAGGT a        E  H  M  F  A  R  H  L  W  A  R  A  G  T  M  G  D  A  I  P    -

GATAATAATGCAGAGTTTTTTCTGCATCCCAATGGTGCACCTCAAAATAAGTTAGCCTCA
  241  ----------+----------+----------+----------+----------+----------+ 300
       CTATTATTACGTCTCAAAAAAGACGTAGGGTTACCACGTGGAGTTTTATTCAATCGGAGT a        D  N  N  A  E  F  F  L  H  P  N  G  A  P  Q  N  K  L  A  S    -

TTTGCTTATTTTCCAACACCTAGTGGTTCTCTTAATACCAGTGATAATCAATTGTTTAAT
  301  ----------+----------+----------+----------+----------+----------+ 360
       AAACGAATAAAAGGTTGTGGATCACCAAGAGAATTATGGTCACTATTAGTTAACAAATTA a        F  A  Y  F  P  T  P  S  G  S  L  N  T  S  D  N  Q  L  F  N    -

AAGCCGTATTGGTTGCGAAAAGCTCAGGGCACCAACAATGGGATGGATCC
  361  ----------+----------+----------+----------+---------+ 410
       TTCGGCATAACCAACGCTTTTCGAGTCCCGTGGTTGTTACCCTACCTAGG a        K  P  Y  W  L  R  K  A  Q  G  T  N  N  G  M  D        -
```

GGATCCATTGAGGATGCGGATATGAGTGATATAGGATTTGGAGCTGTGAATTTTAGCACT
    1   ----------+----------+----------+----------+----------+----------+  60
        CCTAGGTAACTCCTACGCCTATACTCACTATATCCTAAACCTCGACACTTAAAATCGTGA a       G  S  I  E  D  A  D  M  S  D  I  G  F  G  A  V  N  F  S  T   -

TTCTCTGAAAGCCGGGCTGATGCACCTTTAGAATTAATCAATTCTATTAGTAAATGGCCT
    61  ----------+----------+----------+----------+----------+----------+  120
        AAGAGACTTTCGGCCCGACTACGTGGAAATCTTAATTAGTTAAGATAATCATTTACCGGA a       F  S  E  S  R  A  D  A  P  L  E  L  I  N  S  I  S  K  W  P   -

GATTTTATTCAAATGTCTAAGGATATTTATGGCGATAGAATGTTTTCTTTGGAAAACGT
    121 ----------+----------+----------+----------+----------+----------+  180
        CTAAAATAAGTTTACAGATTCCTATAAATACCGCTATCTTACAAAAAGAAACCTTTTGCA a       D  F  I  Q  M  S  K  D  I  Y  G  D  R  M  F  F  F  G  K  R   -

GAGCAGATGTATGCAAGACACACATTTTGTAAAGATGGTGCTGTGGGAGATGCTATTCCA
    181 ----------+----------+----------+----------+----------+----------+  240
        CTCGTCTACATACGTTCTGTGTGTAAAACATTTCTACCACGACACCCTCTACGATAAGGT a       E  Q  M  Y  A  R  H  T  F  C  K  D  G  A  V  G  D  A  I  P   -

GAAAATTTAAATAATGATGAGGATGTTCATCATAGGTTTTTATTAAATCCTAAGCCTGAC
    241 ----------+----------+----------+----------+----------+----------+  300
        CTTTTAAATTTATTACTACTCCTACAAGTAGTATCCAAAAATAATTTAGGATTCGGACTG a       E  N  L  N  N  D  E  D  V  H  H  R  F  L  L  N  P  K  P  D   -

GCACCACCATATTCAAACTTAGGAAACAGTACTTACTTTCCTATGCCAAGTGGTTCATTA
    301 ----------+----------+----------+----------+----------+----------+  360
        CGTGGTGGTATAAGTTTGAATCCTTTGTCATGAATGAAAGGATACGGTTCACCAAGTAAT a       A  P  P  Y  S  N  L  G  N  S  T  Y  F  P  M  P  S  G  S  L   -

GTTAGTAGTGAAACTCAATTATTTAACAGACCATTTTGGCTACATCGAGCACAGGGCACC
    361 ----------+----------+----------+----------+----------+----------+  420
        CAATCATCACTTTGAGTTAATAAATTGTCTGGTAAAACCGATGTAGCTCGTGTCCCGTGG a       V  S  S  E  T  Q  L  F  N  R  P  F  W  L  H  R  A  Q  G  T   -

AATAACGGCATGGATCC
    421 ----------+------- 437
        TTATTGCCGTACCTAGG a       N  N  G  M  D   -
```

GGATCCATGGAGGATGGTGAAATGGGCGACATAGGCTTTGGAGCCTTTAATTTTAAAGCC
    1 ---------+---------+---------+---------+---------+---------+ 60
      CCTAGGTACCTCCTACCACTTTACCCGCTGTATCCGAAACCTCGGAAATTAAAATTTCGG a    G  S  M  E  D  G  E  M  G  D  I  G  F  G  A  F  N  F  K  A   -

CTACAGAAAGATCGTGCTGGTGTTAGTTTAGATTTAGTTGATACATTCAGTATATGGCCA
   61 ---------+---------+---------+---------+---------+---------+ 120
      GATGTCTTTCTAGCACGACCACAATCAAATCTAAATCAACTATGTAAGTCATATACCGGT a    L  Q  K  D  R  A  G  V  S  L  D  L  V  D  T  F  S  I  W  P   -

GACTTTTTAAAAATGACTAATGATATATATGGTGACAGTATCTTTTTTTATGGTAAAAGA
  121 ---------+---------+---------+---------+---------+---------+ 180
      CTGAAAAATTTTTACTGATTACTATATATACCACTGTCATAGAAAAAAATACCATTTTCT a    D  F  L  K  M  T  N  D  I  Y  G  D  S  I  F  F  Y  G  K  R   -

GAACAGCTATTTAGTAGACACTTGTGGGCCCGCGCAGGAACGGCTGGAGATGCCATTCCA
  181 ---------+---------+---------+---------+---------+---------+ 240
      CTTGTCGATAAATCATCTGTGAACACCCGGGCGCGTCCTTGCCGACCTCTACGGTAAGGT a    E  Q  L  F  S  R  H  L  W  A  R  A  G  T  A  G  D  A  I  P   -

TCTCCTGATAACAAAAATCTAATATTTCAGGGTGATGATGCAGTGCCACAAAAGACTGCT
  241 ---------+---------+---------+---------+---------+---------+ 300
      AGAGGACTATTGTTTTTAGATTATAAAGTCCCACTACTACGTCACGGTGTTTTCTGACGA a    S  P  D  N  K  N  L  I  F  Q  G  D  D  A  V  P  Q  K  T  A   -

GGGTCTTTTACTTATTTTAGTGCCCCTAGTGGGTCATTAACAACTAGTGATTCTCAGTTA
  301 ---------+---------+---------+---------+---------+---------+ 360
      CCCAGAAAATGAATAAAATCACGGGGATCACCCAGTAATTGTTGATCACTAAGAGTCAAT a    G  S  F  T  Y  F  S  A  P  S  G  S  L  T  T  S  D  S  Q  L   -

TTTAATAGGCCATATTGGTTAAGAAGAGCTCAAGGTACCAACAACGGTGTGGATCC
  361 ---------+---------+---------+---------+---------+------ 416
      AAATTATCCGGTATAACCAATTCTTCTCGAGTTCCATGGTTGTTGCCACACCTAGG a    F  N  R  P  Y  W  L  R  R  A  Q  G  T  N  N  G  V  D      -
```

FIG. 6 vs204-4

```
     GGATCCATGGAGGACGGTGAGATGAGTGATACAGGTTTTGGTGCTATGAATTTTGATAAT
  1  ----------+----------+----------+----------+----------+----------+  60
     CCTAGGTACCTCCTGCCACTCTACTCACTATGTCCAAAACCACGATACTTAAAACTATTA
```
a   G  S  M  E  D  G  E  M  S  D  T  G  F  G  A  M  N  F  D  N    -

```
     CTATGCGAGGACAGAGCTTCATTTCCTTTAGACATTATAAATGAGACCTCCAAGTGGCCT
 61  ----------+----------+----------+----------+----------+----------+  120
     GATACGCTCCTGTCTCGAAGTAAAGGAAATCTGTAATATTTACTCTGGAGGTTCACCGGA
```
a   L  C  E  D  R  A  S  F  P  L  D  I  I  N  E  T  S  K  W  P    -

```
     GATTTTCTAAAAATGAATAAAGATCCTTATGGAGATCATATATTTTTCTTTGGTTTACGA
121  ----------+----------+----------+----------+----------+----------+  180
     CTAAAAGATTTTTACTTATTTCTAGGAATACCTCTAGTATATAAAAAGAAACCAAATGCT
```
a   D  F  L  K  M  N  K  D  P  Y  G  D  H  I  F  F  F  G  L  R    -

```
     GAGCAGTTATATTCCAGACATCATGGTGCTCGGGGAGGAAAAATGGGAGATACTATTCCA
181  ----------+----------+----------+----------+----------+----------+  240
     CTCGTCAATATAAGGTCTGTAGTACCACGAGCCCCTCCTTTTTACCCTCTATGATAAGGT
```
a   E  Q  L  Y  S  R  H  H  G  A  R  G  G  K  M  G  D  T  I  P    -

```
     GAAAATACAGCAGGCGAATATTATTATCCTCCTACTGATGGTGCTCAGCAAAATATAGGT
241  ----------+----------+----------+----------+----------+----------+  300
     CTTTTATGTCGTCCGCTTATAATAATAGGAGGATGACTACCACGAGTCGTTTTATATCCA
```
a   E  N  T  A  G  E  Y  Y  Y  P  P  T  D  G  A  Q  Q  N  I  G    -

```
     TCACATATTTATTTCAATACTGTTAGTGGATCTTTAACATCTTCAGAAACTCAGATATTT
301  ----------+----------+----------+----------+----------+----------+  360
     AGTGTATAAATAAAGTTATGACAATCACCTAGAAATTGTAGAAGTCTTTGAGTCTATAAA
```
a   S  H  I  Y  F  N  T  V  S  G  S  L  T  S  S  E  T  Q  I  F    -

```
     AATAGGCCATATTTTTTACAACGTGCACAGGGCACAAACAACGGAGTGGATCC
361  ----------+----------+----------+----------+----------+---    413
     TTATCCGGTATAAAAAATGTTGCACGTGTCCCGTGTTTGTTGCCTCACCTAGG
```
a   N  R  P  Y  F  L  Q  R  A  Q  G  T  N  N  G  V  D    -

FIG. 7 vs205-1

```
       GGATCCATTCAAGATGGGGATATGTGCGATATTGGCTTTGGAGCAGCCAATTTTAAAGCA
    1  ----------+----------+----------+----------+----------+----------+  60
       CCTAGGTAAGTTCTACCCCTATACACGCTATAACCGAAACCTCGTCGGTTAAAATTTCGT a      G  S  I  Q  D  G  D  M  C  D  I  G  F  G  A  A  N  F  K  A    -

TTACAGCAAGATAAATCAGGTGTTCCTTTAGATATTGTTGACAGTATATGTAAATGGCCA
   61  ----------+----------+----------+----------+----------+----------+  120
       AATGTCGTTCTATTTAGTCCACAAGGAAATCTATAACAACTGTCATATACATTTACCGGT a      L  Q  Q  D  K  S  G  V  P  L  D  I  V  D  S  I  C  K  W  P    -

GATATTATTAAAATGGAGCAAGAAATATATGGAGACAGATTATTTTTCTTTACTAAACGT
  121  ----------+----------+----------+----------+----------+----------+  180
       CTATAATAATTTTACCTCGTTCTTTATATACCTCTGTCTAATAAAAAGAAATGATTTGCA a      D  I  I  K  M  E  Q  E  I  Y  G  D  R  L  F  F  F  T  K  R    -

GAGCAAGCTTATGCCAGGCATTATTTCGCTCGTGCAGGAATTAATGGTGATTCTTTACCA
  181  ----------+----------+----------+----------+----------+----------+  240
       CTCGTTCGAATACGGTCCGTAATAAAGCGAGCACGTCCTTAATTACCACTAAGAAATGGT a      E  Q  A  Y  A  R  H  Y  F  A  R  A  G  I  N  G  D  S  L  P    -

GATGCAATGAAACCAGGAGAATATTATCTCTCTCCTAAGTTGGGAGATGAGCAAGTACCC
  241  ----------+----------+----------+----------+----------+----------+  300
       CTACGTTACTTTGGTCCTCTTATAATAGAGAGAGGATTCAACCCTCTACTCGTTCATGGG a      D  A  M  K  P  G  E  Y  Y  L  S  P  K  L  G  D  E  Q  V  P    -

CAGAAAGACTTAGGATCGCATATTTATTTTCCTACAGTTAGTGGTTCTTTGGTTTCTAGT
  301  ----------+----------+----------+----------+----------+----------+  360
       GTCTTTCTGAATCCTAGCGTATAAATAAAAGGATGTCAATCACCAAGAAACCAAAGATCA a      Q  K  D  L  G  S  H  I  Y  F  P  T  V  S  G  S  L  V  S  S    -

GAAAATCAGTTATTTAACAGACCATATTGGTTGCAGAAATCTCAGGGCACAAACAACGGC
  361  ----------+----------+----------+----------+----------+----------+  420
       CTTTTAGTCAATAAATTGTCTGGTATAACCAACGTCTTTAGAGTCCCGTGTTTGTTGCCG a      E  N  Q  L  F  N  R  P  Y  W  L  Q  K  S  Q  G  T  N  N  G    -

GTGGATCC
  421  --------  428
       CACCTAGG a      V  D                                                            -
```

GGATCCCTGGAAGATGGTGAAATGGGAGATATTGGGTTTGGTGCAGCAAATTTTAAAACG
     1  ---------+---------+---------+---------+---------+---------+  60
        CCTAGGGACCTTCTACCACTTTACCCTCTATAACCCAAACCACGTCGTTTAAAATTTTGC a         G  S  L  E  D  G  E  M  G  D  I  G  F  G  A  A  N  F  K  T    -

TTACAAAAGGACAGAGCCGGAGTCAGCTTAGATTTAGTAGACACTTTTAGCATTTGGCCT
    61  ---------+---------+---------+---------+---------+---------+ 120
        AATGTTTTCCTGTCTCGGCCTCAGTCGAATCTAAATCATCTGTGAAAATCGTAAACCGGA a         L  Q  K  D  R  A  G  V  S  L  D  L  V  D  T  F  S  I  W  P    -

GACTTTTTAAAAATGACTAATGATATTTACGGAGATAGTATGTTTTTCTTTGGAAAACGT
   121  ---------+---------+---------+---------+---------+---------+ 180
        CTGAAAAATTTTTACTGATTACTATAAATGCCTCTATCATACAAAAGAAACCTTTTGCA a         D  F  L  K  M  T  N  D  I  Y  G  D  S  M  F  F  F  G  K  R    -

GAGCAGCTCTTTGGCAGACATCTTTGGACAAGAGCAGGTACTCCCGGCGATGCAATTCCT
   181  ---------+---------+---------+---------+---------+---------+ 240
        CTCGTCGAGAAACCGTCTGTAGAAACCTGTTCTCGTCCATGAGGGCCGCTACGTTAAGGA a         E  Q  L  F  G  R  H  L  W  T  R  A  G  T  P  G  D  A  I  P    -

ACTCCAGAAAATATAAACTTAATATTTCCAGCTGATGATGGCACTAGTCAAAAGGATGCA
   241  ---------+---------+---------+---------+---------+---------+ 300
        TGAGGTCTTTTATATTTGAATTATAAAGGTCGACTACTACCGTGATCAGTTTTCCTACGT a         T  P  E  N  I  N  L  I  F  P  A  D  D  G  T  S  Q  K  D  A    -

GGGTCTTTCACTTACTTTACTTCAGCTAGTGGATCTCTTAATACTAGCGATTCACAATTA
   301  ---------+---------+---------+---------+---------+---------+ 360
        CCCAGAAAGTGAATGAAATGAAGTCGATCACCTAGAGAATTATGATCGCTAAGTGTTAAT a         G  S  F  T  Y  F  T  S  A  S  G  S  L  N  T  S  D  S  Q  L    -

TTTAATAGACCTTACTGGCTTCGACGTGCACAAGGCACAAACAATGGCGTGGATCC
   361  ---------+---------+---------+---------+---------+------  416
        AAATTATCTGGAATGACCGAAGCTGCACGTGTTCCGTGTTTGTTACCGCACCTAGG a         F  N  R  P  Y  W  L  R  R  A  Q  G  T  N  N  G  V  D        -
```

FIG. 9 vs207-22

```
    GGATCCCTAGAGGATGGGGAGATGGGTGATATAGGATTTGGTGCTGCTAATTTTGCTAAG
  1 ---------+---------+---------+---------+---------+---------+ 60
    CCTAGGGATCTCCTACCCCTCTACCCACTATATCCTAAACCACGACGATTAAAACGATTC a    G  S  L  E  D  G  E  M  G  D  I  G  F  G  A  A  N  F  A  K   -

CTTATGCAAGATAGAGCTGGTGTACCTCTGGAATTAATAGATAGTATTAGTATATGGCCA
 61 ---------+---------+---------+---------+---------+---------+ 120
    GAATACGTTCTATCTCGACCACATGGAGACCTTAATTATCTATCATAATCATATACCGGT a    L  M  Q  D  R  A  G  V  P  L  E  L  I  D  S  I  S  I  W  P   -

GATTTTCTAAAAATGACAAAGGATATTTATGGAAATGAAGTATTTTTCTTTGGAAAACGC
121 ---------+---------+---------+---------+---------+---------+ 180
    CTAAAAGATTTTTACTGTTTCCTATAAATACCTTTACTTCATAAAAAGAAACCTTTTGCG a    D  F  L  K  M  T  K  D  I  Y  G  N  E  V  F  F  F  G  K  R   -

GAGCAATGTTATGCTCGCCATTTATTTGCCAGAGCTGGTACTATGGGAGAACCAGTACCT
181 ---------+---------+---------+---------+---------+---------+ 240
    CTCGTTACAATACGAGCGGTAAATAAACGGTCTCGACCATGATACCCTCTTGGTCATGGA a    E  Q  C  Y  A  R  H  L  F  A  R  A  G  T  M  G  E  P  V  P   -

AATGAGACTAATGGAGTAAATTTTATAAATGCAAAACCAGGAGATCCAAATCCCAGGAGC
241 ---------+---------+---------+---------+---------+---------+ 300
    TTACTCTGATTACCTCATTTAAAATATTTACGTTTTGGTCCTCTAGGTTTAGGGTCCTCG a    N  E  T  N  G  V  N  F  I  N  A  K  P  G  D  P  N  P  R  S   -

GCTCATATGGGTTCTTCAGTATACTTTGCAACACCTAGTGGCTCCCTTAATACCAGTGAT
301 ---------+---------+---------+---------+---------+---------+ 360
    CGAGTATACCCAAGAAGTCATATGAAACGTTGTGGATCACCGAGGGAATTATGGTCACTA a    A  H  M  G  S  S  V  Y  F  A  T  P  S  G  S  L  N  T  S  D   -

TCACAAATATTTAACAGACCTTATTGGTTACGACGGGCTCAAGGAACGAACAACGGCATG
361 ---------+---------+---------+---------+---------+---------+ 420
    AGTGTTTATAAATTGTCTGGAATAACCAATGCTGCCCGAGTTCCTTGCTTGTTGCCGTAC a    S  Q  I  F  N  R  P  Y  W  L  R  R  A  Q  G  T  N  N  G  M   -

GATCC
421 ----- 425
    CTAGG a    D   -
```

GGATCCCTTGAGGATGGGGAAATGATAGATACAGGCTATGGTGCCATGGACTTTCGTACA
    1  ----------+---------+---------+---------+---------+---------+ 60
       CCTAGGGAACTCCTACCCCTTTACTATCTATGTCCGATACCACGGTACCTGAAAGCATGT a        G  S  L  E  D  G  E  M  I  D  T  G  Y  G  A  M  D  F  R  T  -

TTGCAGGAAACCAAAAGTGAGGTACCACTAGATATTTGCCAATCCGTGTGTAAATATCCT
   61  ----------+---------+---------+---------+---------+---------+ 120
       AACGTCCTTTGGTTTTCACTCCATGGTGATCTATAAACGGTTAGGCACACATTTATAGGA a        L  Q  E  T  K  S  E  V  P  L  D  I  C  Q  S  V  C  K  Y  P  -

GATTATTTGCAGATGTCTGCTGATGTATATGGGGACAGTATGTTTTTTTGTTTGCGCAAG
  121  ----------+---------+---------+---------+---------+---------+ 180
       CTAATAAACGTCTACAGACGACTACATATACCCCTGTCATACAAAAAAACAAACGCGTTC a        D  Y  L  Q  M  S  A  D  V  Y  G  D  S  M  F  F  C  L  R  K  -

GAACAGTTGTTTGCCAGGCACTTTTGGAATAGAGGTGGCATGGTGGGCGACACAATACCT
  181  ----------+---------+---------+---------+---------+---------+ 240
       CTTGTCAACAAACGGTCCGTGAAAACCTTATCTCCACCGTACCACCCGCTGTGTTATGGA a        E  Q  L  F  A  R  H  F  W  N  R  G  G  M  V  G  D  T  I  P  -

TCAGAGTTATATATTAAAGGCACGGATATACGTGAGCGTCCTGGTACTCATGTATATTCC
  241  ----------+---------+---------+---------+---------+---------+ 300
       AGTCTCAATATATAATTTCCGTGCCTATATGCACTCGCAGGACCATGAGTACATATAAGG a        S  E  L  Y  I  K  G  T  D  I  R  E  R  P  G  T  H  V  Y  S  -

CCTTCCCCAAGTGGCTCTATGGTCTCTTCTGATTCCCAGTTGTTTAATAAGCCCTATTGG
  301  ----------+---------+---------+---------+---------+---------+ 360
       GGAAGGGGTTCACCGAGATACCAGAGAAGACTAAGGGTCAACAAATTATTCGGGATAACC a        P  S  P  S  G  S  M  V  S  S  D  S  Q  L  F  N  K  P  Y  W  -

TTGCATAAGGCCCAAGGCCACAATAACGGGATGGATCC
  361  ----------+---------+---------+-------- 398
       AACGTATTCCGGGTTCCGGTGTTATTGCCCTACCTAGG a        L  H  K  A  Q  G  H  N  N  G  M  D     -
```

US 6,562,597 B2

PAPILLOMA VIRUSES, AGENTS FOR DETECTING THEM AND FOR TREATING DISEASES CAUSED BY SUCH VIRUSES

This is a division of and claims priority to U.S. patent application Ser. No. 09/628,099 filed on May 25, 2000, now U.S. Pat. No. 6,368,832, which is a division of and claims priority to U.S. patent application Ser. No. 09/000,266, filed on Oct. 19, 1998, now U.S. Pat. No. 6,322,795, which is a Rule 371 national stage application of PCT/DE96/01369 filed on Jul. 19, 1996, which claims priority to German application No. P 195 26 386.3 filed on Jul. 19, 1995, each of which are incorporated herein by reference.

I. FIELD OF THE INVENTION

This invention relates to a DNA coding for a peptide of a papilloma virus major capsid protein. Moreover, this invention deals with a papilloma virus genome containing such a DNA. In addition, this invention concerns proteins coded by the papilloma virus genome and virus-like particles as well as antibodies directed against them and their use for diagnosis, treatment and vaccination.

II. BACKGROUND OF THE INVENTION

It is known that papilloma viruses infect the epithelium of human beings and animals. Human papilloma viruses (hereinafter referred to as HP viruses) are found in benign epithelial neoplasms, e.g warts, condylomas in the genital zone, and malignant epithelial neoplasms, e.g carcinomas of the skin and the uterus. Zur Hausen, 1989, *Cancer Research* 49:4677–4681. HP viruses are also considered for the growth of malignant tumors in the respiratory tract. Zur Hausen, 1976, *Cancer Research* 36:530. Besides, HP viruses are considered at least jointly responsible for the growth of squamous carcinomas of the lung. Syrjänen, 1980, *Lung* 158:131–142.

Papilloma viruses have an icosahedral capsid without envelope in which a circular, double-stranded DNA molecule of about 7900 bp is present. The capsid comprises a major capsid protein (L1) and a minor capsid protein (L2). Both proteins, coexpressed or L1 expressed alone, result in vitro in the formation of virus-like particles Kirnbauer et al., 1993, *Journal of Virology* 67:6929–6936.

Papilloma viruses cannot be proliferated in monolayer cell culture. Therefore, their characterization is extremely difficult, the detection of papilloma viruses already creating considerable problems. This applies especially to papilloma viruses in carcinomas of the skin. A reliable detection thereof and thus well-calculated steps taken thereagainst are not possible by now.

Thus, it is the object of the present invention to provide a product by which papilloma viruses can be detected, particularly in carcinomas of the skin. Furthermore, a product should be provided to be able to take therapeutic steps against these papilloma viruses.

III. SUMMARY OF THE INVENTION

This invention relates to a DNA coding for a peptide of a papilloma virus major capsid protein. Moreover, this invention deals with a papilloma virus genome containing such a DNA. Furthermore, this invention concerns proteins coded by the papilloma virus genome and virus-like particles as well as antibodies directed thereagainst and the use thereof for diagnosis, treatment and vaccination.

IV. BRIEF DESCRIPTION OF THE DRAWINGS

FIG. 1 shows the base sequence (SEQ ID NOS:1 and 3) and the amino acid sequence (SEQ ID NO:2), derived therefrom, of a DNA coding for a peptide of L1 of a papilloma virus. This DNA was deposited as plasmid VS 19-6 with DSM (*Deutsche Sammlung von Mikroorganismen und Zellkulturen* [German-type collection of microorganisms and cell cultures]) under DSM 10104 on Jul. 11, 1995.

FIG. 2 shows the base sequence (SEQ ID NOS:4 and 6) and the amino acid sequence (SEQ ID NO:5), derived therefrom, of a DNA coding for a peptide of L1 of a papilloma virus. This DNA was deposited as plasmid VS200-1 with DSM under DSM 10096 on Jul. 11, 1995.

FIG. 3 shows the base sequence (SEQ ID NOS:7 and 9) and the amino acid sequence (SEQ ID NO:8), derived therefrom, of a DNA coding for a peptide of L1 of a papilloma virus. This DNA was deposited as plasmid VS201-1 with DSM under DSM 10097 on Jul. 11, 1995.

FIG. 4 shows the base sequence (SEQ ID NOS:10 and 12) and the amino acid sequence (SEQ ID NO: 11), derived therefrom, of a DNA coding for a peptide of L1 of a papilloma virus. This DNA was deposited as plasmid VS202-8 with DSM under DSM 10098 on Jul. 11, 1995.

FIG. 5 shows the base sequence (SEQ ID NOS:13 and 15) and the amino acid sequence (SEQ ID NO: 14), derived therefrom, of a DNA coding for a peptide of L1of a papilloma virus. This DNA was deposited as plasmid VS203-2with DSM under DSM 10099 on Jul. 11, 1995.

FIG. 6 shows the base sequence (SEQ ID NOS:16 and 18) and the amino acid sequence (SEQ ID NO: 17), derived therefrom, of a DNA coding for a peptide of L1 of a papilloma virus. This DNA was deposited as plasmid VS204-4 with DSM under DSM 10100 on Jul. 11, 1995.

FIG. 7 shows the base sequence (SEQ ID NOS: 19 and 21) and the amino acid sequence (SEQ ID NO:20), derived therefrom, of a DNA coding for a peptide of L1 of a papilloma virus. This DNA was deposited as plasmid VS205-1 with DSM with DSM under DSM 10101 on Jul. 11, 1995.

FIG. 8 shows the base sequence (SEQ ID NOS:22 and 24) and the amino acid sequence (SEQ ID NO:23), derived therefrom, of a DNA coding for a peptide of L1 of a papilloma virus. This DNA was deposited as plasmid VS206-2 with DSM under DSM 10109 on Jul. 13, 1995.

FIG. 9 shows the base sequence (SEQ ID NOS:25 and 27) and the amino acid sequence (SEQ ID NO:26), derived therefrom, of a DNA coding for a peptide of L1 of a papilloma virus. This DNA was deposited as plasmid VS207-22 with DSM under DSM 10102 on Jul. 11, 1995.

FIG. 10 shows the base sequence (SEQ ID NOS:28 and 30) and the amino acid sequence (SEQ ID NO:29), derived therefrom, of a DNA coding for a peptide of L1 of a papilloma virus. This DNA was deposited as plasmid VS208-1 with DSM under DSM 10103 on Jul. 11, 1995.

V. DETAILED DESCRIPTION OF THE INVENTION

It is the object of the present invention to provide a product by which papilloma viruses can be detected, particularly in carcinomas of the skin. Furthermore, a product is provided which enables to take therapeutic steps against these papilloma viruses.

Accordingly, the subject matter of the invention relates to a DNA coding for a peptide of a papilloma virus major capsid protein (L1), the peptide comprising the amino acid sequence of FIG. 1, FIG. 2, FIG. 3, FIG. 4, FIG. 5, FIG. 6, FIG. 7, FIG. 8, FIG. 9 or FIG. 10 or an amino acid sequence differing therefrom by one or more amino acids.

A further subject matter of the invention relates to a DNA coding for a peptide of a papilloma virus major capsid protein, the DNA comprising the base sequence of FIG. 1, FIG. 2, FIG. 3, FIG. 4, FIG. 5, FIG. 6, FIG. 7, FIG. 8, FIG. 9 or FIG. 10 or a base sequence differing therefrom by one or more base pairs.

The above DNA has the following sequence homology with respect to known papilloma viruses:

| | |
|---|---|
| DNA of FIG. 1: | 69.1% with respect to HP virus 65 |
| DNA of FIG. 2: | 80.7% with respect to HP virus 24 |
| DNA of FIG. 3: | 69.4% with respect to HP virus 48 |
| DNA of FIG. 4: | 66.3% with respect to HP virus 48 |
| DNA of FIG. 5: | 66.9% with respect to HP virus 65 |
| DNA of FIG. 6: | 66.4% with respect to HP virus 65 |
| DNA of FIG. 7: | 69.1% with respect to HP virus 4 |
| DNA of FIG. 8: | 68.7% with respect to HP virus 48 |
| DNA of FIG. 9: | 76.6% with respect to HP virus 48 |
| DNA of FIG. 10: | 81.8% with respect to HP virus 68 |

According to the invention, the above DNA can be present in a vector and expression vector, respectively. A person skilled in the art is familiar with examples thereof. In the case of an expression vector for *E. coli*, these are e.g pGEMEX, pUC derivatives, pGEM-T and pGEX-2T. For the expression in yeast e.g. pY100 and Ycpad1 have to be mentioned, while for the expression in animal cells e.g. pKCR, pEF-BOS, cDM8 and pCEV4 have to be indicated.

The person skilled in the art knows suitable cells to express the above DNA present in an expression vector. Examples of such cells comprise the *E. coli* strains HB101, DH1, x1776, JM101, JM 109, and XL1-Blue, the yeast strain *Saccharomyces cerevisiae* and the animal cells L, NH-3T3, FM3A, CHO, COS, Vero, and HeLa.

The person skilled in the art knows in which way the above DNA has to be inserted in an expression vector. He is also familiar with the fact that the above DNA can be inserted in connection with a DNA coding for another protein and peptide, respectively, so that the above DNA can be expressed in the form of a fusion protein.

A further subject matter of the invention relates to a papilloma virus genome which comprises the above DNA. The expression "papilloma virus genome" also comprises an incomplete genome, i.e. fragments of a papilloma virus genome, which comprise the above DNA. This may be e.g a DNA coding for L1 or a portion thereof.

A common process can be used for the provision of the above papilloma virus genome, which comprises the following processing steps:

(a) isolation of the total DNA from a biopsy of epithelial neoplasm, (b) hybridization of the total DNA of (a) with the above DNA so as to detect a papilloma virus genome included in the total DNA of (a), and (c) cloning of the total DNA of (a) containing the papilloma virus genome, in a vector and optionally subcloning the resulting clone, all processing steps originating from common DNA recombination technique.

As far as the isolation, hybridization and cloning of cell DNA is concerned, reference is made by way of supplement to Sambrook et al., *Molecular Cloning A Laboratory Manual*, second edition, Cold Spring Harbor Laboratory (1989).

The expression "epithelial neoplasm" comprises any neoplasms of epithelium in man and animal. Examples of such neoplasms are warts, condylomas in the genital zone and carcinomas of the skin. The latter are used preferably to isolate the above papilloma virus genome.

The expression "vector" comprises any vectors suitable for cloning chromosomal DNA and extrachromosomal DNA, respectively. Examples of such vectors are cosmids such as pWE15 and Super Cos1, and phages such as λ-phages, e.g. λZAP expression vector, λZAPII vector and λgt10 vector. In the present case, λ-phages are used preferably. The above vectors are known and obtainable from the company of Stratagene.

Papilloma virus genomes according to the invention may be present in integrated form in chromosomal DNA or in extrachromosomal fashion. The person skilled in the art is familiar with processes serving the clarification thereof. He also knows processes serving for finding out the optimum restriction enzymes for cloning the papilloma virus genomes. He will orient himself by genomes of known papilloma viruses. In particular, the person skilled in the art will pay corresponding attention to the above-mentioned HP viruses.

The provision of a papilloma virus genome referred to as VS19-6 is described by way of example. For this purpose, the total DNA is isolated from a biopsy of a squamous cell carcinoma, cleaved by BamHI and separated eletrophoretically in an agarose gel. The agarose gel is then subjected to a blotting method so as to transfer the DNA to a nitrocellulose membrane. It is inserted in a hybridization method in which the DNA of FIG. 1 is used as labeled sample, optionally in combination with a DNA of HP virus 65. Hybridization with the papilloma virus DNA present in the total DNA is obtained.

Moreover, the above total DNA cleaved by BamHI is cloned in a λ-phage. The corresponding clones, i.e. the clones containing the papilloma virus DNA are identified by hybridization with the DNA of FIG. 1, optionally in combination with a DNA of the HP virus 65. The insert of these clones is then subjected to a further cloning in a plasmid vector so as to obtain a clone which contains the papilloma virus genome VS19-6-G. The genome is confirmed by sequencing.

Further papilloma virus genomes are provided analogously. They are designated in accordance with the DNAs used for their provision, namely by: VS200-1-G, VS201-1-G, VS202-8-G, VS203-2-G, VS204-4-G, VS205-1-G, VS206-2-G, VS 207-22-G and VS208-1-G, respectively.

A further subject matter of the invention relates to a protein which is coded by the above papilloma virus genome. Such a protein is e.g. a major capsid protein (L1) or a minor capsid protein (L2). An above protein is prepared as usual. The preparation of L1 and L2, respectively, of the papilloma virus genome VS19-6-G is described by way of example. For this purpose, the HP virus 65 related to the DNA of FIG. 1 is used. The full sequence and the position of individual DNA regions coding for proteins are known in connection therewith. These DNAs are identified on the papilloma virus genome VS19-6-G by parallel restriction cleavages of both genomes and subsequent hybridization with various fragments concerning the DNA encoding L1 and L2, respectively. They are confirmed by sequencing. The DNA coding for L1 is referred to as VS19-6-G-L1 DNA and the DNA coding for L2 is referred to as VS19-6-G-L2 DNA.

Furthermore, the DNA coding for L1 and L2, respectively, is inserted in an expression vector. Examples thereof are mentioned above for *E. coli,* yeast and animal cells. In this connection, reference is made to the vector pGEX-2T as regards the expression in *E. coli* by way of supplement. Kimbauer et al., supra. Having inserted the VS19-6-G-L1 DNA and VS19-6-G-L2 DNA, one obtains pGEX-2T-VS19-6-G-L1 and pGEX-2T-VS19-6-G-L2, respectively. After transforming *E. coli,* these expression vectors express a glutathione S transferase L1 fusion protein and glutathione S transferase L2 fusion protein, respectively. The proteins are purified as usual.

The bacculovirus system and vaccinia virus system, respectively, is mentioned for a further expression of the above DNA encoding L1 and L2, respectively. Expression vectors usable for this purpose are e.g. pEV mod. and pSynwtVI- for the bacculovirus system. Kirnbauer et al., supra. Especially vectors with the vaccinia virus "early" (p7.5 k) promoter and "late" (Psynth, p11K) promoter, respectively, have to be mentioned for the vaccinia virus system. Hagensee et al., 1993, *Journal of Virology* 67:315-322. The bacculovirus system is preferred in the present case. Having inserted the above DNA encoding L1 and L2, respectively, in pEV mod., one obtains pEVmod.-VS19-6-G-L1 and pEVmod.-VS19-6-G-L2, respectively.

The former expression vector as such or both expression vectors jointly lead to the formation of virus-like particles after infection of SF-9 insect cells. In the former case, such a particle comprises an L1 protein, while in the latter case, it contains an L2 protein in addition to an L1 protein.

A virus-like particle of the latter case is also obtained by inserting the above VS 19-6-G-L1 and VS19-6-G-L2 DNAs jointly in the expression vector pSynwtVI- and using the resulting pSynwtVI-VS19-6-G-L1/L2 for the infection of SF-9 insect cells. The above virus-like particles are purified as usual. They also represent a subject matter of the invention.

A further subject matter of the invention relates to an antibody directed against an above protein and virus-like particle, respectively. The preparation thereof is made as usual. It is described by way of example for the preparation of an antibody which is directed against a virus-like particle comprising L1 of VS19-6-G. For this purpose, the virus-like particle is injected subcutaneously into BALB/c mice. This injection is repeated at intervals of 3 weeks each. About 2 weeks after the last injection, the serum containing the antibody is isolated and tested as usual.

In a preferred embodiment, the antibody is a monoclonal antibody. For its preparation, spleen cells are removed from the mice after the above fourth injection and fused with myeloma cells as usual. The further cloning also takes place according to known methods.

By means of the present invention, it is possible to detect papilloma viruses, particularly in carcinomas of the skin. For this purpose, the DNA according to the invention can be used as such or when comprised by a further DNA. The latter may also be a papilloma virus genome or a portion thereof.

The present invention also enables the provision of formerly unknown papilloma viruses. They are found especially in carcinomas of the skin. In addition, the invention supplies proteins and virus-like particles which originate from these papilloma viruses. Moreover, antibodies are provided which are directed against these proteins and particles, respectively.

The present invention also enables to take diagnostic and therapeutic steps in the case of papilloma virus diseases. Moreover, it supplies the possibility of building up a vaccine against papilloma virus infections. Thus, the present invention represents a break-through in the field of papilloma virus research.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

VI. EXAMPLES

A. Example 1

Identification of the Papilloma Virus Genome VS19-6-G

The total DNA is isolated from a biopsy of a squamous cell carcinoma of an immuno-suppressed person. 10 µg of this DNA are cleaved by the restriction enzyme BamHI and separated electrophoretically in a 0.5% agarose gel. At the same time, 10 µg of the above DNA, which was not cleaved, is also separated. The agarose gel is subjected to a blotting method so as to transfer the DNA from the agarose gel to a nitrocellulose membrane. It is employed in a hybridization method in which the above DNA of FIG. 1 is used in combination with the HP virus-65 DNA as $^{32}$P-labeled sample. Hybridization with the blotted DNA is obtained.

The person skilled in the field of DNA recombination technique is familiar with the above methods. Reference is made to Sambrook et al., supra, by way of supplement.

B. Example 2

Cloning of the Papilloma Virus Genome VS19-6-G.

The biopsy DNA obtained from Example 1 is cleaved by the restriction enzyme BamHI. The resulting fragments are used in a ligase reaction in which the dephosphorylated vector λZAP express cleaved by BamHI is also present. The resulting recombinant DNA molecules are packed in bacteriophages, and they are used for infecting bacteria. For these processing steps, the ZAP express vector kit offered by the company of Stratagene is used. The resulting phage plaques are then subjected to a hybridization process which uses the $^{32}$P-labeled DNA of FIG. 1 employed in Example 1 in combination with $^{32}$P-labeled HP virus-65 DNA. Hybridization with corresponding phage plaques is obtained. The BamHI fragments of VS19-6-G are isolated therefrom and used in a further ligase reaction together with a BamHI-cleaved, dephosphorylated plasmid vector, pBluescript. The resulting recombinant DNA molecules are used for transforming bacteria, *E. coli* XL1-Blue. By restriction cleavages and hybridization with the above DNA samples, respectively, a bacterial clone containing the papilloma virus genome VS19-6-G is identified. The plasmid of this bacterial clone is referred to as pBlue-VS19-6-G.

All references cited within the body of the instant specification are hereby incorporated by reference in their entirety.

What is claimed:

1. A polypeptide encoded by the nucleotide sequence of SEQ ID NO:4, SEQ ID NO:19, SEQ ID NO:22, SEQ ID NO:25, or SEQ ID NO:28.

2. A polypeptide encoded by a polynucleotide hybridizing to the complement of the nucleotide sequence of SEQ ID NO:4, SEQ ID NO: 19, SEQ ID NO:22, SEQ ID NO:25, or SEQ ID NO:28, wherein the polynucleotide has at least 90% identity to the nucleotide sequence of SEQ ID NO:4, SEQ ID NO: 19, SEQ ID NO:22, SEQ ID NO:25, or SEQ ID NO:28.

3. An isolated polypeptide consisting of the amino acid sequence selected from SEQ ID NO:4, SEQ ID NO: 19, SEQ ID NO:22, SEQ ID NO:25, or SEQ ID NO:28.

4. A composition comprising the polypeptide of any one of claims 1, 2, or 3 as reagent for diagnosis, treatment and/or vaccination, and a pharmaceutically acceptable carrier.

5. A pharmaceutical composition comprising the polypeptide of any one of claims 1, 2, or 3 and a pharmaceutically acceptable carrier.

6. A method of vaccinating a subject in need against papillomavirus, comprising administering to the subject the composition of claim 4.

7. A method of vaccinating a subject in need against papillomavirus, comprising administering to the subject the composition of claim 5.

8. A method of treating a subject in need against papillomavirus, comprising administering to the subject the composition of claim 4.

9. A method of treating a subject in need against papillomavirus, comprising administering to the subject the composition of claim 5.

10. A diagnostic kit to detect papillomavirus infection wherein the kit comprises the polypeptide of any one of claims 1, 2, or 3 as reagent for diagnosis.

* * * * *

SEQUENCE LISTING

<160> NUMBER OF SEQ ID NOS: 30

<210> SEQ ID NO 1
<211> LENGTH: 419
<212> TYPE: DNA
<213> ORGANISM: Papilloma virus
<220> FEATURE:
<221> NAME/KEY: CDS
<222> LOCATION: (1)...(417)

<400> SEQUENCE: 1

```
gga tcc atg cag gat ggt gac atg tgt gat ata gga ttc gga gct tgc      48
Gly Ser Met Gln Asp Gly Asp Met Cys Asp Ile Gly Phe Gly Ala Cys
  1               5                  10                  15 aat ttc agg gca ttt cag caa gat agg tca ggt gtt cct tta gat ata      96
Asn Phe Arg Ala Phe Gln Gln Asp Arg Ser Gly Val Pro Leu Asp Ile
             20                  25                  30 gta gat agt act tgc aag tat cca gac ttt ttg aaa atg aca aaa gac     144
Val Asp Ser Thr Cys Lys Tyr Pro Asp Phe Leu Lys Met Thr Lys Asp
         35                  40                  45 aag tat ggt gat gaa tgc ttc ttt ttt ggt cgt cga gag cag ttg tat     192
Lys Tyr Gly Asp Glu Cys Phe Phe Phe Gly Arg Arg Glu Gln Leu Tyr
     50                  55                  60 gca agg cat tat ttt acc aga gca ggc aca ata ggt gat tct att cca     240
Ala Arg His Tyr Phe Thr Arg Ala Gly Thr Ile Gly Asp Ser Ile Pro
 65                  70                  75                  80 acg cca tat cag gaa tct gaa ttt tac aga tct cca cag gat agc cag     288
Thr Pro Tyr Gln Glu Ser Glu Phe Tyr Arg Ser Pro Gln Asp Ser Gln
                 85                  90                  95 gct cag aat aat gtg gat tct cac att tat gta gcc act cct agt ggt     336
Ala Gln Asn Asn Val Asp Ser His Ile Tyr Val Ala Thr Pro Ser Gly
            100                 105                 110 tct tta act agc agt gat gct cag ctg ttt aac aga cct tat tgg ctc     384
Ser Leu Thr Ser Ser Asp Ala Gln Leu Phe Asn Arg Pro Tyr Trp Leu
        115                 120                 125 caa aat gct caa ggt acc aat aac gga atg gat cc                      419
Gln Asn Ala Gln Gly Thr Asn Asn Gly Met Asp
    130                 135
```

<210> SEQ ID NO 2
<211> LENGTH: 139
<212> TYPE: PRT
<213> ORGANISM: Papilloma virus

<400> SEQUENCE: 2

```
Gly Ser Met Gln Asp Gly Asp Met Cys Asp Ile Gly Phe Gly Ala Cys
  1               5                  10                  15

Asn Phe Arg Ala Phe Gln Gln Asp Arg Ser Gly Val Pro Leu Asp Ile
             20                  25                  30

Val Asp Ser Thr Cys Lys Tyr Pro Asp Phe Leu Lys Met Thr Lys Asp
         35                  40                  45

Lys Tyr Gly Asp Glu Cys Phe Phe Phe Gly Arg Arg Glu Gln Leu Tyr
     50                  55                  60

Ala Arg His Tyr Phe Thr Arg Ala Gly Thr Ile Gly Asp Ser Ile Pro
 65                  70                  75                  80

Thr Pro Tyr Gln Glu Ser Glu Phe Tyr Arg Ser Pro Gln Asp Ser Gln
                 85                  90                  95

Ala Gln Asn Asn Val Asp Ser His Ile Tyr Val Ala Thr Pro Ser Gly
            100                 105                 110
```

```
Ser Leu Thr Ser Ser Asp Ala Gln Leu Phe Asn Arg Pro Tyr Trp Leu
        115                 120                 125

Gln Asn Ala Gln Gly Thr Asn Asn Gly Met Asp
    130                 135

<210> SEQ ID NO 3
<211> LENGTH: 419
<212> TYPE: DNA
<213> ORGANISM: Papilloma virus

<400> SEQUENCE: 3
ggatccattc cgttattggt accttgagca ttttggagcc aataaggtct gttaaacagc      60
tgagcatcac tgctagttaa agaaccacta ggagtggcta cataaatgtg agaatccaca     120
ttattctgag cctggctatc ctgtggagat ctgtaaaatt cagattcctg atatggcgtt     180
ggaatagaat cacctattgt gcctgctctg gtaaaataat gccttgcata caactgctct     240
cgacgaccaa aaagaagca ttcatcacca tacttgtctt ttgtcatttt caaaaagtct      300
ggatacttgc aagtactatc tactatatct aaaggaacac ctgacctatc ttgctgaaat     360
gccctgaaat tgcaagctcc gaatcctata tcacacatgt caccatcctg catggatcc     419

<210> SEQ ID NO 4
<211> LENGTH: 434
<212> TYPE: DNA
<213> ORGANISM: Papilloma virus
<220> FEATURE:
<221> NAME/KEY: CDS
<222> LOCATION: (1)...(432)

<400> SEQUENCE: 4
```

| gga tcc atg gag gac ggt gag atg gca gac ata gga tat ggt aat ctt | 48 |
|---|---|
| Gly Ser Met Glu Asp Gly Glu Met Ala Asp Ile Gly Tyr Gly Asn Leu | |
| 1               5                  10                  15 | |

| aat ttt aaa gct tta cag gaa aat agg cct gat gtt agt ctt gat att | 96 |
|---|---|
| Asn Phe Lys Ala Leu Gln Glu Asn Arg Pro Asp Val Ser Leu Asp Ile | |
|         20                  25                  30 | |

| gtc aat gaa acc tgc aaa tat cca gat ttt ttg aag atg caa aat gat | 144 |
|---|---|
| Val Asn Glu Thr Cys Lys Tyr Pro Asp Phe Leu Lys Met Gln Asn Asp | |
|     35                  40                  45 | |

| gtt tat gga gac tcc tgt ttc ttt ttt gct cgt aga gag caa tgt tat | 192 |
|---|---|
| Val Tyr Gly Asp Ser Cys Phe Phe Phe Ala Arg Arg Glu Gln Cys Tyr | |
| 50                  55                  60 | |

| gcc aga cac ttt ttt gta aga ggt ggc aac gta ggg gat gac att cct | 240 |
|---|---|
| Ala Arg His Phe Phe Val Arg Gly Gly Asn Val Gly Asp Asp Ile Pro | |
| 65                  70                  75                  80 | |

| ggt gaa caa ata gac gca ggc aca tat aaa aat gat ttt tac att cca | 288 |
|---|---|
| Gly Glu Gln Ile Asp Ala Gly Thr Tyr Lys Asn Asp Phe Tyr Ile Pro | |
|             85                  90                  95 | |

| gga gca tca ggt cag aca caa aat aaa ata ggt aac tcc atg tat ttc | 336 |
|---|---|
| Gly Ala Ser Gly Gln Thr Gln Asn Lys Ile Gly Asn Ser Met Tyr Phe | |
|         100                 105                 110 | |

| cca aca gtt agt ggc tca tta gtg tct agt gat gct cag ctg ttt aat | 384 |
|---|---|
| Pro Thr Val Ser Gly Ser Leu Val Ser Ser Asp Ala Gln Leu Phe Asn | |
|     115                 120                 125 | |

| agg ccc tac tgg ctc caa cgc gca cag ggc cac aac aac ggc gtg gat | 432 |
|---|---|
| Arg Pro Tyr Trp Leu Gln Arg Ala Gln Gly His Asn Asn Gly Val Asp | |
| 130                 135                 140 | |

| cc | 434 |

```
<210> SEQ ID NO 5
<211> LENGTH: 144
<212> TYPE: PRT
<213> ORGANISM: Papilloma virus

<400> SEQUENCE: 5

Gly Ser Met Glu Asp Gly Glu Met Ala Asp Ile Gly Tyr Gly Asn Leu
  1               5                  10                  15

Asn Phe Lys Ala Leu Gln Glu Asn Arg Pro Asp Val Ser Leu Asp Ile
             20                  25                  30

Val Asn Glu Thr Cys Lys Tyr Pro Asp Phe Leu Lys Met Gln Asn Asp
         35                  40                  45

Val Tyr Gly Asp Ser Cys Phe Phe Ala Arg Arg Glu Gln Cys Tyr
     50                  55                  60

Ala Arg His Phe Phe Val Arg Gly Gly Asn Val Gly Asp Asp Ile Pro
 65                  70                  75                  80

Gly Glu Gln Ile Asp Ala Gly Thr Tyr Lys Asn Asp Phe Tyr Ile Pro
                 85                  90                  95

Gly Ala Ser Gly Gln Thr Gln Asn Lys Ile Gly Asn Ser Met Tyr Phe
            100                 105                 110

Pro Thr Val Ser Gly Ser Leu Val Ser Ser Asp Ala Gln Leu Phe Asn
        115                 120                 125

Arg Pro Tyr Trp Leu Gln Arg Ala Gln Gly His Asn Asn Gly Val Asp
    130                 135                 140

<210> SEQ ID NO 6
<211> LENGTH: 434
<212> TYPE: DNA
<213> ORGANISM: Papilloma virus

<400> SEQUENCE: 6
ggatccacgc cgttgttgtg gccctgtgcg cgttggagcc agtagggcct attaaacagc     60
tgagcatcac tagacactaa tgagccacta actgttggga atacatggca gttacctatt    120
ttattttgtg tctgacctga tgctcctgga atgtaaaaat cattttttata tgtgcctgcg    180 tctatttgtt caccaggaat gtcatcccct acgttgccac ctcttacaaa aaagtgtctg    240
gcataacatt gctctctacg agcaaaaaag aaacaggagt ctccataaac atcattttgc    300
atcttcaaaa aatctggata tttgcaggtt tcattgacaa tatcaagact aacatcaggc    360
ctattttcct gtaaagcttt aaaattaaga ttaccatatc ctatgtctgc catctcaccg    420
tcctccatgg atcc                                                      434

<210> SEQ ID NO 7
<211> LENGTH: 410
<212> TYPE: DNA
<213> ORGANISM: Papilloma virus
<220> FEATURE:
<221> NAME/KEY: CDS
<222> LOCATION: (1)...(408)

<400> SEQUENCE: 7 gga tcc cta gag gat ggt gat atg ggt gat ata gga ttt ggg cat gct     48
Gly Ser Leu Glu Asp Gly Asp Met Gly Asp Ile Gly Phe Gly His Ala
  1               5                  10                  15 aat ttt agc cgt tta caa gaa gat aaa gca ggt gtg cca tta gaa tta     96
Asn Phe Ser Arg Leu Gln Glu Asp Lys Ala Gly Val Pro Leu Glu Leu
             20                  25                  30 gtg gac act ttt agt ata tgg cct gac ttt tta cgc atg acc agt gat    144
Val Asp Thr Phe Ser Ile Trp Pro Asp Phe Leu Arg Met Thr Ser Asp
```

```
                35                    40                   45
ata tat gga gat gct gtg ttt ttt tgg gga aag cga gaa cat atg ttt     192
Ile Tyr Gly Asp Ala Val Phe Phe Trp Gly Lys Arg Glu His Met Phe
     50                   55                   60 gcc aga cat tta tgg gca aga gct gga act atg ggc gac gct att cca     240
Ala Arg His Leu Trp Ala Arg Ala Gly Thr Met Gly Asp Ala Ile Pro
 65                  70                   75                   80 gat aat aat gca gag ttt ttt ctg cat ccc aat ggt gca cct caa aat     288
Asp Asn Asn Ala Glu Phe Phe Leu His Pro Asn Gly Ala Pro Gln Asn
                 85                   90                   95 aag tta gcc tca ttt gct tat ttt cca aca cct agt ggt tct ctt aat     336
Lys Leu Ala Ser Phe Ala Tyr Phe Pro Thr Pro Ser Gly Ser Leu Asn
                100                  105                  110 acc agt gat aat caa ttg ttt aat aag ccg tat tgg ttg cga aaa gct     384
Thr Ser Asp Asn Gln Leu Phe Asn Lys Pro Tyr Trp Leu Arg Lys Ala
            115                  120                  125 cag ggc acc aac aat ggg atg gat cc                                   410
Gln Gly Thr Asn Asn Gly Met Asp
        130                  135

<210> SEQ ID NO 8
<211> LENGTH: 136
<212> TYPE: PRT
<213> ORGANISM: Papilloma virus

<400> SEQUENCE: 8

Gly Ser Leu Glu Asp Gly Asp Met Gly Asp Ile Gly Phe Gly His Ala
 1               5                   10                  15

Asn Phe Ser Arg Leu Gln Glu Asp Lys Ala Gly Val Pro Leu Glu Leu
                20                  25                  30

Val Asp Thr Phe Ser Ile Trp Pro Asp Phe Leu Arg Met Thr Ser Asp
            35                  40                  45

Ile Tyr Gly Asp Ala Val Phe Phe Trp Gly Lys Arg Glu His Met Phe
     50                   55                   60

Ala Arg His Leu Trp Ala Arg Ala Gly Thr Met Gly Asp Ala Ile Pro
 65                  70                   75                   80

Asp Asn Asn Ala Glu Phe Phe Leu His Pro Asn Gly Ala Pro Gln Asn
                 85                   90                   95

Lys Leu Ala Ser Phe Ala Tyr Phe Pro Thr Pro Ser Gly Ser Leu Asn
                100                  105                  110

Thr Ser Asp Asn Gln Leu Phe Asn Lys Pro Tyr Trp Leu Arg Lys Ala
            115                  120                  125

Gln Gly Thr Asn Asn Gly Met Asp
        130                  135

<210> SEQ ID NO 9
<211> LENGTH: 410
<212> TYPE: DNA
<213> ORGANISM: Papilloma virus

<400> SEQUENCE: 9
ggatccatcc cattgttggt gccctgagct tttcgcaacc aatacggctt attaaacaat      60
tgattatcac tggtattaag agaaccacta ggtgttggaa aataagcaaa tgaggctaac     120 ttatttttgag gtgcaccatt gggatgcaga aaaaactctg cattattatc tggaatagcg     180
tcgcccatag ttccagctct tgcccataaa tgtctggcaa acatatgttc tcgctttccc     240
caaaaaaaca cagcatctcc atatatatca ctggtcatgc gtaaaaagtc aggccatata     300
```

-continued

```
ctaaaagtgt ccactaattc taatggcaca cctgctttat cttcttgtaa acggctaaaa      360
ttagcatgcc caaatcctat atcacccata tcaccatcct ctagggatcc                 410

<210> SEQ ID NO 10
<211> LENGTH: 437
<212> TYPE: DNA
<213> ORGANISM: Papilloma virus
<220> FEATURE:
<221> NAME/KEY: CDS
<222> LOCATION: (1)...(435)

<400> SEQUENCE: 10 gga tcc att gag gat gcg gat atg agt gat ata gga ttt gga gct gtg       48
Gly Ser Ile Glu Asp Ala Asp Met Ser Asp Ile Gly Phe Gly Ala Val
1               5                  10                  15 aat ttt agc act ttc tct gaa agc cgg gct gat gca cct tta gaa tta       96
Asn Phe Ser Thr Phe Ser Glu Ser Arg Ala Asp Ala Pro Leu Glu Leu
                20                  25                  30 atc aat tct att agt aaa tgg cct gat ttt att caa atg tct aag gat      144
Ile Asn Ser Ile Ser Lys Trp Pro Asp Phe Ile Gln Met Ser Lys Asp
        35                  40                  45 att tat ggc gat aga atg ttt ttc ttt gga aaa cgt gag cag atg tat      192
Ile Tyr Gly Asp Arg Met Phe Phe Phe Gly Lys Arg Glu Gln Met Tyr
    50                  55                  60 gca aga cac aca ttt tgt aaa gat ggt gct gtg gga gat gct att cca      240
Ala Arg His Thr Phe Cys Lys Asp Gly Ala Val Gly Asp Ala Ile Pro
65                  70                  75                  80 gaa aat tta aat aat gat gag gat gtt cat cat agg ttt tta tta aat      288
Glu Asn Leu Asn Asn Asp Glu Asp Val His His Arg Phe Leu Leu Asn
                85                  90                  95 cct aag cct gac gca cca cca tat tca aac tta gga aac agt act tac      336
Pro Lys Pro Asp Ala Pro Pro Tyr Ser Asn Leu Gly Asn Ser Thr Tyr
                100                 105                 110 ttt cct atg cca agt ggt tca tta gtt agt agt gaa act caa tta ttt      384
Phe Pro Met Pro Ser Gly Ser Leu Val Ser Ser Glu Thr Gln Leu Phe
        115                 120                 125 aac aga cca ttt tgg cta cat cga gca cag ggc acc aat aac ggc atg      432
Asn Arg Pro Phe Trp Leu His Arg Ala Gln Gly Thr Asn Asn Gly Met
    130                 135                 140 gat cc                                                                437
Asp
145

<210> SEQ ID NO 11
<211> LENGTH: 145
<212> TYPE: PRT
<213> ORGANISM: Papilloma virus

<400> SEQUENCE: 11

Gly Ser Ile Glu Asp Ala Asp Met Ser Asp Ile Gly Phe Gly Ala Val
1               5                  10                  15

Asn Phe Ser Thr Phe Ser Glu Ser Arg Ala Asp Ala Pro Leu Glu Leu
                20                  25                  30

Ile Asn Ser Ile Ser Lys Trp Pro Asp Phe Ile Gln Met Ser Lys Asp
        35                  40                  45

Ile Tyr Gly Asp Arg Met Phe Phe Phe Gly Lys Arg Glu Gln Met Tyr
    50                  55                  60

Ala Arg His Thr Phe Cys Lys Asp Gly Ala Val Gly Asp Ala Ile Pro
65                  70                  75                  80

Glu Asn Leu Asn Asn Asp Glu Asp Val His His Arg Phe Leu Leu Asn
```

```
                        85                  90                  95
Pro Lys Pro Asp Ala Pro Pro Tyr Ser Asn Leu Gly Asn Ser Thr Tyr
                100                 105                 110

Phe Pro Met Pro Ser Gly Ser Leu Val Ser Ser Glu Thr Gln Leu Phe
            115                 120                 125

Asn Arg Pro Phe Trp Leu His Arg Ala Gln Gly Thr Asn Asn Gly Met
    130                 135                 140

Asp
145

<210> SEQ ID NO 12
<211> LENGTH: 437
<212> TYPE: DNA
<213> ORGANISM: Papilloma virus

<400> SEQUENCE: 12
ggatccatgc cgttattggt gccctgtgct cgatgtagcc aaaatggtct gttaaataat      60
tgagtttcac tactaactaa tgaaccactt ggcataggaa agtaagtact gtttcctaag     120
tttgaatatg gtggtgcgtc aggcttagga tttaataaaa acctatgatg aacatcctca     180
tcattattta aattttctgg aatagcatct cccacagcac catctttaca aaatgtgtgt     240
cttgcataca tctgctcacg ttttccaaag aaaaacattc tatcgccata aatatcctta     300
gacatttgaa taaatcagg ccatttacta atagaattga ttaattctaa aggtgcatca     360
gcccggcttt cagagaaagt gctaaaattc acagctccaa atcctatatc actcatatcc     420
gcatcctcaa tggatcc                                                    437

<210> SEQ ID NO 13
<211> LENGTH: 416
<212> TYPE: DNA
<213> ORGANISM: Papilloma virus
<220> FEATURE:
<221> NAME/KEY: CDS
<222> LOCATION: (1)...(414)

<400> SEQUENCE: 13 gga tcc atg gag gat ggt gaa atg ggc gac ata ggc ttt gga gcc ttt       48
Gly Ser Met Glu Asp Gly Glu Met Gly Asp Ile Gly Phe Gly Ala Phe
  1               5                  10                  15 aat ttt aaa gcc cta cag aaa gat cgt gct ggt gtt agt tta gat tta       96
Asn Phe Lys Ala Leu Gln Lys Asp Arg Ala Gly Val Ser Leu Asp Leu
                20                  25                  30 gtt gat aca ttc agt ata tgg cca gac ttt tta aaa atg act aat gat      144
Val Asp Thr Phe Ser Ile Trp Pro Asp Phe Leu Lys Met Thr Asn Asp
            35                  40                  45 ata tat ggt gac agt atc ttt ttt tat ggt aaa aga gaa cag cta ttt      192
Ile Tyr Gly Asp Ser Ile Phe Phe Tyr Gly Lys Arg Glu Gln Leu Phe
        50                  55                  60 agt aga cac ttg tgg gcc cgc gca gga acg gct gga gat gcc att cca      240
Ser Arg His Leu Trp Ala Arg Ala Gly Thr Ala Gly Asp Ala Ile Pro
    65                  70                  75                  80 tct cct gat aac aaa aat cta ata ttt cag ggt gat gat gca gtg cca      288
Ser Pro Asp Asn Lys Asn Leu Ile Phe Gln Gly Asp Asp Ala Val Pro
                85                  90                  95 caa aag act gct ggg tct ttt act tat ttt agt gcc cct agt ggg tca      336
Gln Lys Thr Ala Gly Ser Phe Thr Tyr Phe Ser Ala Pro Ser Gly Ser
                100                 105                 110 tta aca act agt gat tct cag tta ttt aat agg cca tat tgg tta aga      384
Leu Thr Thr Ser Asp Ser Gln Leu Phe Asn Arg Pro Tyr Trp Leu Arg
```

```
                 115                 120                 125
aga gct caa ggt acc aac aac ggt gtg gat cc                              416
Arg Ala Gln Gly Thr Asn Asn Gly Val Asp
        130                 135
```

<210> SEQ ID NO 14
<211> LENGTH: 138
<212> TYPE: PRT
<213> ORGANISM: Papilloma virus

<400> SEQUENCE: 14

```
Gly Ser Met Glu Asp Gly Glu Met Gly Asp Ile Gly Phe Gly Ala Phe
1               5                   10                  15

Asn Phe Lys Ala Leu Gln Lys Asp Arg Ala Gly Val Ser Leu Asp Leu
            20                  25                  30

Val Asp Thr Phe Ser Ile Trp Pro Asp Phe Leu Lys Met Thr Asn Asp
        35                  40                  45

Ile Tyr Gly Asp Ser Ile Phe Phe Tyr Gly Lys Arg Glu Gln Leu Phe
    50                  55                  60

Ser Arg His Leu Trp Ala Arg Ala Gly Thr Ala Gly Asp Ala Ile Pro
65                  70                  75                  80

Ser Pro Asp Asn Lys Asn Leu Ile Phe Gln Gly Asp Asp Ala Val Pro
                85                  90                  95

Gln Lys Thr Ala Gly Ser Phe Thr Tyr Phe Ser Ala Pro Ser Gly Ser
            100                 105                 110

Leu Thr Thr Ser Asp Ser Gln Leu Phe Asn Arg Pro Tyr Trp Leu Arg
        115                 120                 125

Arg Ala Gln Gly Thr Asn Asn Gly Val Asp
    130                 135
```

<210> SEQ ID NO 15
<211> LENGTH: 416
<212> TYPE: DNA
<213> ORGANISM: Papilloma virus

<400> SEQUENCE: 15

```
ggatccacac cgttgttggt accttgagct cttcttaacc aatatggcct attaaataac      60
tgagaatcac tagttgttaa tgacccacta ggggcactaa aataagtaaa agacccagca     120
gtcttttgtg gcactgcatc atcaccctga aatattagat ttttgttatc aggagatgga     180
atggcatctc cagccgttcc tgcgcgggcc cacaagtgtc tactaaatag ctgttctctt     240
ttaccataaa aaagatact gtcaccatat atatcattag tcatttttaa aaagtctggc      300
catatactga atgtatcaac taaatctaaa ctaacaccag cacgatcttt ctgtagggct     360
ttaaaattaa aggctccaaa gcctatgtcg cccatttcac catcctccat ggatcc         416
```

<210> SEQ ID NO 16
<211> LENGTH: 413
<212> TYPE: DNA
<213> ORGANISM: Papilloma virus
<220> FEATURE:
<221> NAME/KEY: CDS
<222> LOCATION: (1)...(411)

<400> SEQUENCE: 16

```
gga tcc atg gag gac ggt gag atg agt gat aca ggt ttt ggt gct atg       48
Gly Ser Met Glu Asp Gly Glu Met Ser Asp Thr Gly Phe Gly Ala Met
1               5                   10                  15 aat ttt gat aat cta tgc gag gac aga gct tca ttt cct tta gac att       96
```

```
                Asn Phe Asp Asn Leu Cys Glu Asp Arg Ala Ser Phe Pro Leu Asp Ile
                                20                  25                  30 ata aat gag acc tcc aag tgg cct gat ttt cta aaa atg aat aaa gat         144
Ile Asn Glu Thr Ser Lys Trp Pro Asp Phe Leu Lys Met Asn Lys Asp
            35                  40                  45 cct tat gga gat cat ata ttt ttc ttt ggt tta cga gag cag tta tat         192
Pro Tyr Gly Asp His Ile Phe Phe Phe Gly Leu Arg Glu Gln Leu Tyr
50                      55                  60 tcc aga cat cat ggt gct cgg gga gga aaa atg gga gat act att cca         240
Ser Arg His His Gly Ala Arg Gly Gly Lys Met Gly Asp Thr Ile Pro
 65                     70                  75                  80 gaa aat aca gca ggc gaa tat tat cct cct act gat ggt gct cag             288
Glu Asn Thr Ala Gly Glu Tyr Tyr Pro Pro Thr Asp Gly Ala Gln
                85                  90                  95 caa aat ata ggt tca cat att tat ttc aat act gtt agt gga tct tta         336
Gln Asn Ile Gly Ser His Ile Tyr Phe Asn Thr Val Ser Gly Ser Leu
            100                 105                 110 aca tct tca gaa act cag ata ttt aat agg cca tat ttt tta caa cgt         384
Thr Ser Ser Glu Thr Gln Ile Phe Asn Arg Pro Tyr Phe Leu Gln Arg
            115                 120                 125 gca cag ggc aca aac aac gga gtg gat cc                                  413
Ala Gln Gly Thr Asn Asn Gly Val Asp
        130                 135

<210> SEQ ID NO 17
<211> LENGTH: 137
<212> TYPE: PRT
<213> ORGANISM: Papilloma virus

<400> SEQUENCE: 17

Gly Ser Met Glu Asp Gly Glu Met Ser Asp Thr Gly Phe Gly Ala Met
1               5                   10                  15

Asn Phe Asp Asn Leu Cys Glu Asp Arg Ala Ser Phe Pro Leu Asp Ile
                20                  25                  30

Ile Asn Glu Thr Ser Lys Trp Pro Asp Phe Leu Lys Met Asn Lys Asp
            35                  40                  45

Pro Tyr Gly Asp His Ile Phe Phe Phe Gly Leu Arg Glu Gln Leu Tyr
50                      55                  60

Ser Arg His His Gly Ala Arg Gly Gly Lys Met Gly Asp Thr Ile Pro
 65                     70                  75                  80

Glu Asn Thr Ala Gly Glu Tyr Tyr Pro Pro Thr Asp Gly Ala Gln
                85                  90                  95

Gln Asn Ile Gly Ser His Ile Tyr Phe Asn Thr Val Ser Gly Ser Leu
            100                 105                 110

Thr Ser Ser Glu Thr Gln Ile Phe Asn Arg Pro Tyr Phe Leu Gln Arg
            115                 120                 125

Ala Gln Gly Thr Asn Asn Gly Val Asp
        130                 135

<210> SEQ ID NO 18
<211> LENGTH: 413
<212> TYPE: DNA
<213> ORGANISM: Papilloma virus

<400> SEQUENCE: 18
ggatccactc cgttgtttgt gccctgtgca cgttgtaaaa aatatggcct attaaatatc       60
tgagtttctg aagatgttaa agatccacta acagtattga aataaatatg tgaacctata      120
ttttgctgag caccatcagt aggaggataa taatattcgc ctgctgtatt ttctggaata     180
```

```
gtatctccca tttttcctcc ccgagcacca tgatgtctgg aatataactg ctctcgtaaa      240
ccaaagaaaa atatatgatc tccataagga tctttattca tttttagaaa atcaggccac      300
ttggaggtct catttataat gtctaaagga aatgaagctc tgtcctcgca tagattatca      360
aaattcatag caccaaaacc tgtatcactc atctcaccgt cctccatgga tcc             413
```

```
<210> SEQ ID NO 19
<211> LENGTH: 428
<212> TYPE: DNA
<213> ORGANISM: Papilloma virus
<220> FEATURE:
<221> NAME/KEY: CDS
<222> LOCATION: (1)...(426)

<400> SEQUENCE: 19
```

| | | | | | | | | | | | | | | | | |
|---|---|---|---|---|---|---|---|---|---|---|---|---|---|---|---|---|
| gga | tcc | att | caa | gat | ggg | gat | atg | tgc | gat | att | ggc | ttt | gga | gca | gcc | 48 |
| Gly | Ser | Ile | Gln | Asp | Gly | Asp | Met | Cys | Asp | Ile | Gly | Phe | Gly | Ala | Ala | |
| 1 | | | | 5 | | | | | 10 | | | | | 15 | | |
| aat | ttt | aaa | gca | tta | cag | caa | gat | aaa | tca | ggt | gtt | cct | tta | gat | att | 96 |
| Asn | Phe | Lys | Ala | Leu | Gln | Gln | Asp | Lys | Ser | Gly | Val | Pro | Leu | Asp | Ile | |
| | | | 20 | | | | | 25 | | | | | 30 | | | |
| gtt | gac | agt | ata | tgt | aaa | tgg | cca | gat | att | att | aaa | atg | gag | caa | gaa | 144 |
| Val | Asp | Ser | Ile | Cys | Lys | Trp | Pro | Asp | Ile | Ile | Lys | Met | Glu | Gln | Glu | |
| | | 35 | | | | | 40 | | | | | 45 | | | | |
| ata | tat | gga | gac | aga | tta | ttt | ttc | ttt | act | aaa | cgt | gag | caa | gct | tat | 192 |
| Ile | Tyr | Gly | Asp | Arg | Leu | Phe | Phe | Phe | Thr | Lys | Arg | Glu | Gln | Ala | Tyr | |
| | 50 | | | | | 55 | | | | | 60 | | | | | |
| gcc | agg | cat | tat | ttc | gct | cgt | gca | gga | att | aat | ggt | gat | tct | tta | cca | 240 |
| Ala | Arg | His | Tyr | Phe | Ala | Arg | Ala | Gly | Ile | Asn | Gly | Asp | Ser | Leu | Pro | |
| 65 | | | | | 70 | | | | | 75 | | | | | 80 | |
| gat | gca | atg | aaa | cca | gga | gaa | tat | tat | ctc | tct | cct | aag | ttg | gga | gat | 288 |
| Asp | Ala | Met | Lys | Pro | Gly | Glu | Tyr | Tyr | Leu | Ser | Pro | Lys | Leu | Gly | Asp | |
| | | | 85 | | | | | 90 | | | | | 95 | | | |
| gag | caa | gta | ccc | cag | aaa | gac | tta | gga | tcg | cat | att | tat | ttt | cct | aca | 336 |
| Glu | Gln | Val | Pro | Gln | Lys | Asp | Leu | Gly | Ser | His | Ile | Tyr | Phe | Pro | Thr | |
| | | 100 | | | | | 105 | | | | | 110 | | | | |
| gtt | agt | ggt | tct | ttg | gtt | tct | agt | gaa | aat | cag | tta | ttt | aac | aga | cca | 384 |
| Val | Ser | Gly | Ser | Leu | Val | Ser | Ser | Glu | Asn | Gln | Leu | Phe | Asn | Arg | Pro | |
| | 115 | | | | | 120 | | | | | 125 | | | | | |
| tat | tgg | ttg | cag | aaa | tct | cag | ggc | aca | aac | aac | ggc | gtg | gat | | | 426 |
| Tyr | Trp | Leu | Gln | Lys | Ser | Gln | Gly | Thr | Asn | Asn | Gly | Val | Asp | | | |
| 130 | | | | | 135 | | | | | 140 | | | | | | |
| cc | | | | | | | | | | | | | | | | 428 |

```
<210> SEQ ID NO 20
<211> LENGTH: 142
<212> TYPE: PRT
<213> ORGANISM: Papilloma virus

<400> SEQUENCE: 20
```

Gly Ser Ile Gln Asp Gly Asp Met Cys Asp Ile Gly Phe Gly Ala Ala
1               5                   10                  15

Asn Phe Lys Ala Leu Gln Gln Asp Lys Ser Gly Val Pro Leu Asp Ile
            20                  25                  30

Val Asp Ser Ile Cys Lys Trp Pro Asp Ile Ile Lys Met Glu Gln Glu
        35                  40                  45

Ile Tyr Gly Asp Arg Leu Phe Phe Phe Thr Lys Arg Glu Gln Ala Tyr
    50                  55                  60

Ala Arg His Tyr Phe Ala Arg Ala Gly Ile Asn Gly Asp Ser Leu Pro

```
                65                  70                  75                  80
Asp Ala Met Lys Pro Gly Glu Tyr Tyr Leu Ser Pro Lys Leu Gly Asp
                        85                  90                  95

Glu Gln Val Pro Gln Lys Asp Leu Gly Ser His Ile Tyr Phe Pro Thr
                100                 105                 110

Val Ser Gly Ser Leu Val Ser Ser Glu Asn Gln Leu Phe Asn Arg Pro
            115                 120                 125

Tyr Trp Leu Gln Lys Ser Gln Gly Thr Asn Asn Gly Val Asp
        130                 135                 140

<210> SEQ ID NO 21
<211> LENGTH: 428
<212> TYPE: DNA
<213> ORGANISM: Papilloma virus

<400> SEQUENCE: 21
ggatccacgc cgttgtttgt gccctgagat ttctgcaacc aatatggtct gttaaataac     60
tgattttcac tagaaaccaa agaaccacta actgtaggaa ataaatatg cgatcctaag    120 tctttctggg gtacttgctc atctcccaac ttaggagaga gataatattc tcctggtttc    180
attgcatctg gtaaagaatc accattaatt cctgcacgag cgaaataatg cctggcataa    240
gcttgctcac gtttagtaaa gaaaaataat ctgtctccat atatttcttg ctccatttta    300
ataatatctg gccatttaca tatactgtca acaatatcta aggaacacc tgatttatct    360 tgctgtaatg ctttaaaatt ggctgctcca aagccaatat cgcacatatc cccatcttga    420
atggatcc                                                            428

<210> SEQ ID NO 22
<211> LENGTH: 416
<212> TYPE: DNA
<213> ORGANISM: Papilloma virus
<220> FEATURE:
<221> NAME/KEY: CDS
<222> LOCATION: (1)...(414)

<400> SEQUENCE: 22 gga tcc ctg gaa gat ggt gaa atg gga gat att ggg ttt ggt gca gca      48
Gly Ser Leu Glu Asp Gly Glu Met Gly Asp Ile Gly Phe Gly Ala Ala
 1                5                   10                  15 aat ttt aaa acg tta caa aag gac aga gcc gga gtc agc tta gat tta      96
Asn Phe Lys Thr Leu Gln Lys Asp Arg Ala Gly Val Ser Leu Asp Leu
                20                  25                  30 gta gac act ttt agc att tgg cct gac ttt tta aaa atg act aat gat     144
Val Asp Thr Phe Ser Ile Trp Pro Asp Phe Leu Lys Met Thr Asn Asp
            35                  40                  45 att tac gga gat agt atg ttt ttc ttt gga aaa cgt gag cag ctc ttt     192
Ile Tyr Gly Asp Ser Met Phe Phe Phe Gly Lys Arg Glu Gln Leu Phe
        50                  55                  60 ggc aga cat ctt tgg aca aga gca ggt act ccc ggc gat gca att cct     240
Gly Arg His Leu Trp Thr Arg Ala Gly Thr Pro Gly Asp Ala Ile Pro
 65                 70                  75                  80 act cca gaa aat ata aac tta ata ttt cca gct gat gat ggc act agt     288
Thr Pro Glu Asn Ile Asn Leu Ile Phe Pro Ala Asp Asp Gly Thr Ser
                85                  90                  95 caa aag gat gca ggg tct ttc act tac ttt act tca gct agt gga tct     336
Gln Lys Asp Ala Gly Ser Phe Thr Tyr Phe Thr Ser Ala Ser Gly Ser
            100                 105                 110 ctt aat act agc gat tca caa tta ttt aat aga cct tac tgg ctt cga     384
Leu Asn Thr Ser Asp Ser Gln Leu Phe Asn Arg Pro Tyr Trp Leu Arg
```

```
                115                 120                 125
cgt gca caa ggc aca aac aat ggc gtg gat cc                                    416
Arg Ala Gln Gly Thr Asn Asn Gly Val Asp
    130                 135
```

<210> SEQ ID NO 23
<211> LENGTH: 138
<212> TYPE: PRT
<213> ORGANISM: Papilloma virus

<400> SEQUENCE: 23

```
Gly Ser Leu Glu Asp Gly Glu Met Gly Asp Ile Gly Phe Gly Ala Ala
  1               5                  10                  15

Asn Phe Lys Thr Leu Gln Lys Asp Arg Ala Gly Val Ser Leu Asp Leu
             20                  25                  30

Val Asp Thr Phe Ser Ile Trp Pro Asp Phe Leu Lys Met Thr Asn Asp
         35                  40                  45

Ile Tyr Gly Asp Ser Met Phe Phe Gly Lys Arg Glu Gln Leu Phe
     50                  55                  60

Gly Arg His Leu Trp Thr Arg Ala Gly Thr Pro Gly Asp Ala Ile Pro
 65                  70                  75                  80

Thr Pro Glu Asn Ile Asn Leu Ile Phe Pro Ala Asp Asp Gly Thr Ser
                 85                  90                  95

Gln Lys Asp Ala Gly Ser Phe Thr Tyr Phe Thr Ser Ala Ser Gly Ser
            100                 105                 110

Leu Asn Thr Ser Asp Ser Gln Leu Phe Asn Arg Pro Tyr Trp Leu Arg
        115                 120                 125

Arg Ala Gln Gly Thr Asn Asn Gly Val Asp
    130                 135
```

<210> SEQ ID NO 24
<211> LENGTH: 416
<212> TYPE: DNA
<213> ORGANISM: Papilloma virus

<400> SEQUENCE: 24

```
ggatccacgc cattgtttgt gccttgtgca cgtcgaagcc agtaaggtct attaaataat        60
tgtgaatcgc tagtattaag agatccacta gctgaagtaa agtaagtgaa agaccctgca       120
tccttttgac tagtgccatc atcagctgga aatattaagt ttatattttc tggagtagga       180
attgcatcgc cgggagtacc tgctcttgtc caaagatgtc tgccaaagag ctgctcacgt       240
tttccaaaga aaacatact atctccgtaa atatcattag tcatttttaa aaagtcaggc        300
caaatgctaa aagtgtctac taaatctaag ctgactccgg ctctgtcctt ttgtaacgtt       360 ttaaatttg ctgcaccaaa cccaatatct cccatttcac catcttccag ggatcc            416
```

<210> SEQ ID NO 25
<211> LENGTH: 425
<212> TYPE: DNA
<213> ORGANISM: Papilloma virus
<220> FEATURE:
<221> NAME/KEY: CDS
<222> LOCATION: (1)...(423)

<400> SEQUENCE: 25

```
gga tcc cta gag gat ggg gag atg ggt gat ata gga ttt ggt gct gct         48
Gly Ser Leu Glu Asp Gly Glu Met Gly Asp Ile Gly Phe Gly Ala Ala
  1               5                  10                  15 aat ttt gct aag ctt atg caa gat aga gct ggt gta cct ctg gaa tta         96
```

```
                Asn Phe Ala Lys Leu Met Gln Asp Arg Ala Gly Val Pro Leu Glu Leu
                             20                  25                  30 ata gat agt att agt ata tgg cca gat ttt cta aaa atg aca aag gat      144
Ile Asp Ser Ile Ser Ile Trp Pro Asp Phe Leu Lys Met Thr Lys Asp
         35                  40                  45 att tat gga aat gaa gta ttt ttc ttt gga aaa cgc gag caa tgt tat      192
Ile Tyr Gly Asn Glu Val Phe Phe Phe Gly Lys Arg Glu Gln Cys Tyr
 50                  55                  60 gct cgc cat tta ttt gcc aga gct ggt act atg gga gaa cca gta cct      240
Ala Arg His Leu Phe Ala Arg Ala Gly Thr Met Gly Glu Pro Val Pro
 65                  70                  75                  80 aat gag act aat gga gta aat ttt ata aat gca aaa cca gga gat cca      288
Asn Glu Thr Asn Gly Val Asn Phe Ile Asn Ala Lys Pro Gly Asp Pro
                 85                  90                  95 aat ccc agg agc gct cat atg ggt tct tca gta tac ttt gca aca cct      336
Asn Pro Arg Ser Ala His Met Gly Ser Ser Val Tyr Phe Ala Thr Pro
             100                 105                 110 agt ggc tcc ctt aat acc agt gat tca caa ata ttt aac aga cct tat      384
Ser Gly Ser Leu Asn Thr Ser Asp Ser Gln Ile Phe Asn Arg Pro Tyr
         115                 120                 125 tgg tta cga cgg gct caa gga acg aac aac ggc atg gat cc               425
Trp Leu Arg Arg Ala Gln Gly Thr Asn Asn Gly Met Asp
 130                 135                 140

<210> SEQ ID NO 26
<211> LENGTH: 141
<212> TYPE: PRT
<213> ORGANISM: Papilloma virus

<400> SEQUENCE: 26

Gly Ser Leu Glu Asp Gly Glu Met Gly Asp Ile Gly Phe Gly Ala Ala
 1               5                  10                  15

Asn Phe Ala Lys Leu Met Gln Asp Arg Ala Gly Val Pro Leu Glu Leu
             20                  25                  30

Ile Asp Ser Ile Ser Ile Trp Pro Asp Phe Leu Lys Met Thr Lys Asp
         35                  40                  45

Ile Tyr Gly Asn Glu Val Phe Phe Phe Gly Lys Arg Glu Gln Cys Tyr
 50                  55                  60

Ala Arg His Leu Phe Ala Arg Ala Gly Thr Met Gly Glu Pro Val Pro
 65                  70                  75                  80

Asn Glu Thr Asn Gly Val Asn Phe Ile Asn Ala Lys Pro Gly Asp Pro
                 85                  90                  95

Asn Pro Arg Ser Ala His Met Gly Ser Ser Val Tyr Phe Ala Thr Pro
             100                 105                 110

Ser Gly Ser Leu Asn Thr Ser Asp Ser Gln Ile Phe Asn Arg Pro Tyr
         115                 120                 125

Trp Leu Arg Arg Ala Gln Gly Thr Asn Asn Gly Met Asp
 130                 135                 140

<210> SEQ ID NO 27
<211> LENGTH: 425
<212> TYPE: DNA
<213> ORGANISM: Papilloma virus

<400> SEQUENCE: 27
ggatccatgc cgttgttcgt tccttgagcc cgtcgtaacc aataaggtct gttaaatatt      60
tgtgaatcac tggtattaag ggagccacta ggtgttgcaa agtatactga agaacccata    120
tgagcgctcc tgggatttgg atctcctggt tttgcattta taaaatttac tccattagtc    180
```

```
tcattaggta ctggttctcc catagtacca gctctggcaa ataaatggcg agcataacat      240
tgctcgcgtt ttccaaagaa aaatacttca tttccataaa tatcctttgt cattttttaga    300 aaatctggcc atatactaat actatctatt aattccagag gtacaccagc tctatcttgc      360
ataagcttag caaaattagc agcaccaaat cctatatcac ccatctcccc atcctctagg      420
gatcc                                                                  425
```

<210> SEQ ID NO 28
<211> LENGTH: 398
<212> TYPE: DNA
<213> ORGANISM: Papilloma virus
<220> FEATURE:
<221> NAME/KEY: CDS
<222> LOCATION: (1)...(396)

<400> SEQUENCE: 28

```
gga tcc ctt gag gat ggg gaa atg ata gat aca ggc tat ggt gcc atg        48
Gly Ser Leu Glu Asp Gly Glu Met Ile Asp Thr Gly Tyr Gly Ala Met
 1               5                  10                  15 gac ttt cgt aca ttg cag gaa acc aaa agt gag gta cca cta gat att        96
Asp Phe Arg Thr Leu Gln Glu Thr Lys Ser Glu Val Pro Leu Asp Ile
             20                  25                  30 tgc caa tcc gtg tgt aaa tat cct gat tat ttg cag atg tct gct gat       144
Cys Gln Ser Val Cys Lys Tyr Pro Asp Tyr Leu Gln Met Ser Ala Asp
         35                  40                  45 gta tat ggg gac agt atg ttt ttt tgt ttg cgc aag gaa cag ttg ttt       192
Val Tyr Gly Asp Ser Met Phe Phe Cys Leu Arg Lys Glu Gln Leu Phe
     50                  55                  60 gcc agg cac ttt tgg aat aga ggt ggc atg gtg ggc gac aca ata cct       240
Ala Arg His Phe Trp Asn Arg Gly Gly Met Val Gly Asp Thr Ile Pro
 65                  70                  75                  80 tca gag tta tat att aaa ggc acg gat ata cgt gag cgt cct ggt act       288
Ser Glu Leu Tyr Ile Lys Gly Thr Asp Ile Arg Glu Arg Pro Gly Thr
                 85                  90                  95 cat gta tat tcc cct tcc cca agt ggc tct atg gtc tct tct gat tcc       336
His Val Tyr Ser Pro Ser Pro Ser Gly Ser Met Val Ser Ser Asp Ser
            100                 105                 110 cag ttg ttt aat aag ccc tat tgg ttg cat aag gcc caa ggc cac aat       384
Gln Leu Phe Asn Lys Pro Tyr Trp Leu His Lys Ala Gln Gly His Asn
        115                 120                 125 aac ggg atg gat cc                                                    398
Asn Gly Met Asp
    130
```

<210> SEQ ID NO 29
<211> LENGTH: 132
<212> TYPE: PRT
<213> ORGANISM: Papilloma virus

<400> SEQUENCE: 29

```
Gly Ser Leu Glu Asp Gly Glu Met Ile Asp Thr Gly Tyr Gly Ala Met
 1               5                  10                  15

Asp Phe Arg Thr Leu Gln Glu Thr Lys Ser Glu Val Pro Leu Asp Ile
             20                  25                  30

Cys Gln Ser Val Cys Lys Tyr Pro Asp Tyr Leu Gln Met Ser Ala Asp
         35                  40                  45

Val Tyr Gly Asp Ser Met Phe Phe Cys Leu Arg Lys Glu Gln Leu Phe
     50                  55                  60

Ala Arg His Phe Trp Asn Arg Gly Gly Met Val Gly Asp Thr Ile Pro
```

```
                      65                  70                  75                  80
Ser Glu Leu Tyr Ile Lys Gly Thr Asp Ile Arg Glu Arg Pro Gly Thr
                85                  90                  95

His Val Tyr Ser Pro Ser Pro Ser Gly Ser Met Val Ser Ser Asp Ser
            100                 105                 110

Gln Leu Phe Asn Lys Pro Tyr Trp Leu His Lys Ala Gln Gly His Asn
        115                 120                 125

Asn Gly Met Asp
    130

<210> SEQ ID NO 30
<211> LENGTH: 398
<212> TYPE: DNA
<213> ORGANISM: Papilloma virus

<400> SEQUENCE: 30
ggatccatcc cgttattgtg gccttgggcc ttatgcaacc aatagggctt attaaacaac      60
tgggaatcag aagagaccat agagccactt ggggaagggg aatatacatg agtaccagga    120
cgctcacgta tatccgtgcc tttaatatat aactctgaag gtattgtgtc gcccaccatg    180
ccacctctat tccaaaagtg cctggcaaac aactgttcct tgcgcaaaca aaaaaacata    240
ctgtccccat atacatcagc agacatctgc aaataatcag gatatttaca cacggattgg    300
caaatatcta gtggtacctc acttttggtt tcctgcaatg tacgaaagtc catggcacca    360
tagcctgtat ctatcatttc cccatcctca agggatcc                            398
```